(12) United States Patent
Bowsher

(10) Patent No.: US 8,042,556 B2
(45) Date of Patent: Oct. 25, 2011

(54) ORAL HYGIENE APPARATUSES

(76) Inventor: M. William Bowsher, Lexington, MA (US)

(*) Notice: Subject to any disclaimer, the term of this patent is extended or adjusted under 35 U.S.C. 154(b) by 688 days.

(21) Appl. No.: 10/810,245

(22) Filed: Mar. 25, 2004

(65) Prior Publication Data

US 2004/0250834 A1 Dec. 16, 2004

Related U.S. Application Data

(60) Provisional application No. 60/457,433, filed on Mar. 25, 2003.

(51) Int. Cl.
*A61C 15/00* (2006.01)
(52) U.S. Cl. ............ 132/323; 132/324; 132/325
(58) Field of Classification Search ............ 132/322, 132/323, 324, 325; 63/15.4, 15.6
See application file for complete search history.

(56) References Cited

U.S. PATENT DOCUMENTS

| | | | |
|---|---|---|---|
| 2,138,626 A | 11/1938 | Copen | |
| 2,438,901 A | 4/1948 | Coxe | |
| 3,696,821 A | 10/1972 | Adams, IV | |
| 3,745,788 A * | 7/1973 | Sullivan | 63/15.6 |
| 3,799,177 A | 3/1974 | Bragg | |
| 3,901,251 A * | 8/1975 | Johnston | 132/325 |
| 4,727,895 A | 3/1988 | Berarducci | |
| 4,926,820 A | 5/1990 | Wearn | |
| 5,060,681 A * | 10/1991 | Westbrook et al. | 132/325 |
| 5,199,452 A * | 4/1993 | Cheng | 132/325 |
| 5,415,188 A * | 5/1995 | Altshuler | 132/325 |
| 5,454,386 A | 10/1995 | Dix | |
| 5,477,871 A * | 12/1995 | Sanchez, Jr. | 132/323 |
| 5,503,168 A * | 4/1996 | Wang | 132/324 |
| 5,573,022 A | 11/1996 | Winters | |
| 5,680,875 A * | 10/1997 | Winters | 132/324 |
| 5,692,532 A | 12/1997 | Gabrovsek | |
| D399,603 S | 10/1998 | Hemsley, Jr. et al. | |
| 5,893,379 A | 4/1999 | Ghamaty-Azimi | |
| 6,131,586 A | 10/2000 | Flanagan | |
| 2001/0049838 A1 | 12/2001 | Fitz | |
| 2002/0078974 A1 | 6/2002 | Kossak et al. | |
| 2002/0106607 A1 | 8/2002 | Horowitz | |
| 2002/0170570 A1 * | 11/2002 | Bergman | 132/322 |
| 2002/0185149 A1 | 12/2002 | Ali | |
| 2003/0106565 A1 | 6/2003 | Andrews | |
| 2004/0163665 A1 * | 8/2004 | Alvarez | 132/322 |

* cited by examiner

*Primary Examiner* — Robyn Doan
(74) *Attorney, Agent, or Firm* — O'Connell Law Firm

(57) ABSTRACT

A dental hygiene apparatus for enabling a flossing of teeth. The apparatus can include a dispensing member and an accumulating member. The dispensing and accumulating members can each comprise a ring with an aperture for receiving a finger. Activating switches can selectively enable a dispensing of dental floss from the dispensing member and a retraction of dental floss relative to the accumulating member. A bobbin within the accumulating member can be rotated by a coil spring that can be rewound. The apertures in the rings can be varied. A floss retaining member can alternatively be retained by a ring, an opposed hook arrangement, or any other arrangement coupled to the dispensing member. Dental floss can be dispensed from a distal end of a post. The dental hygiene apparatus can further include as part of a unified system a finger shield arrangement, which can comprise first and second tubular members.

10 Claims, 23 Drawing Sheets

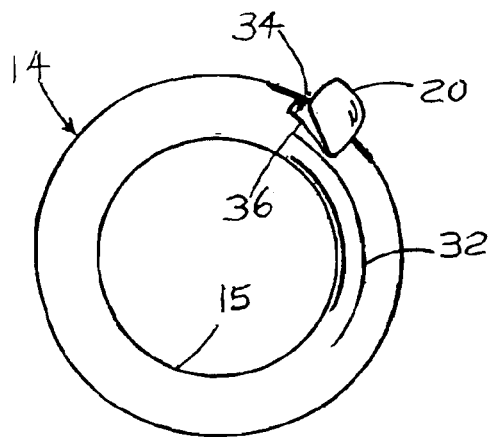
FIG. 3A
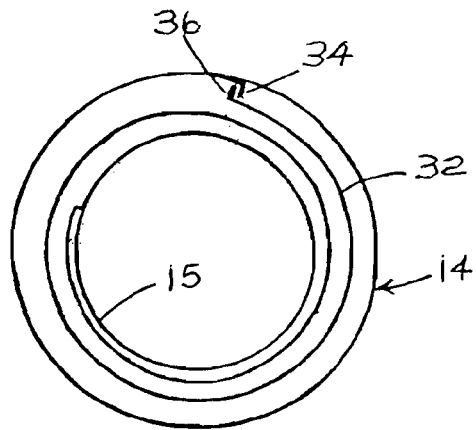
FIG. 3B
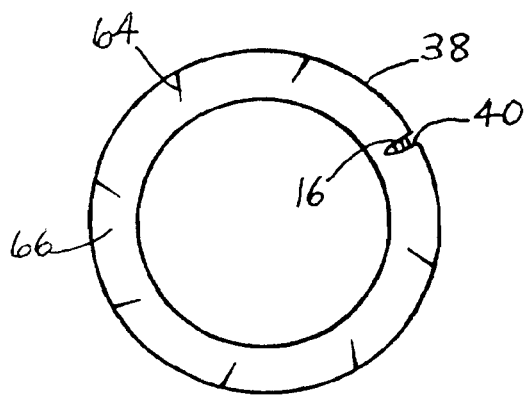
FIG. 3C
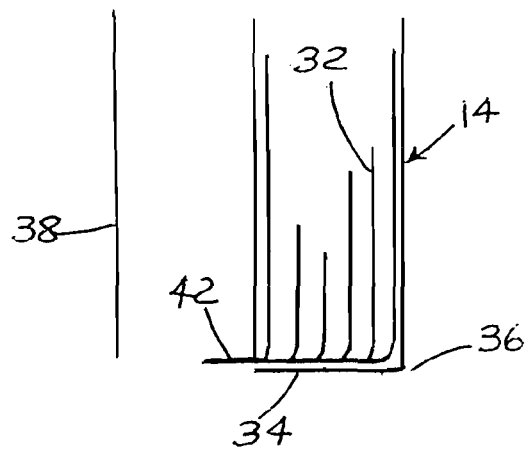
FIG. 3D
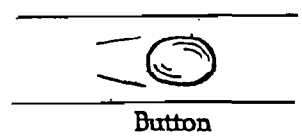
Button

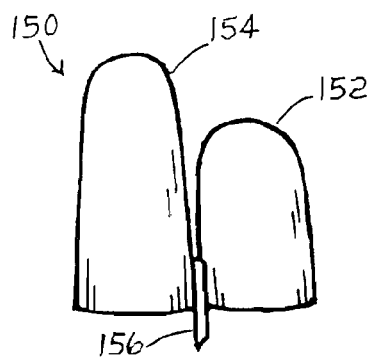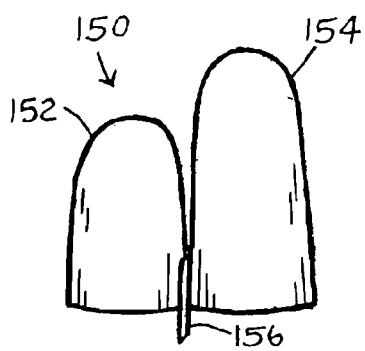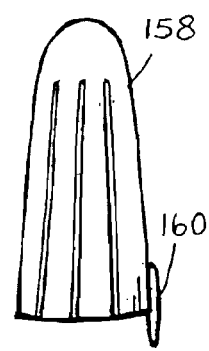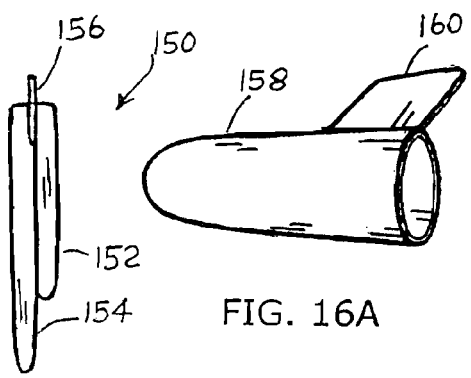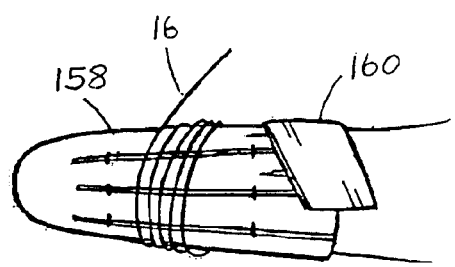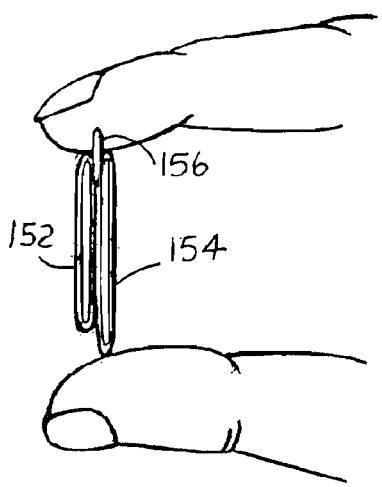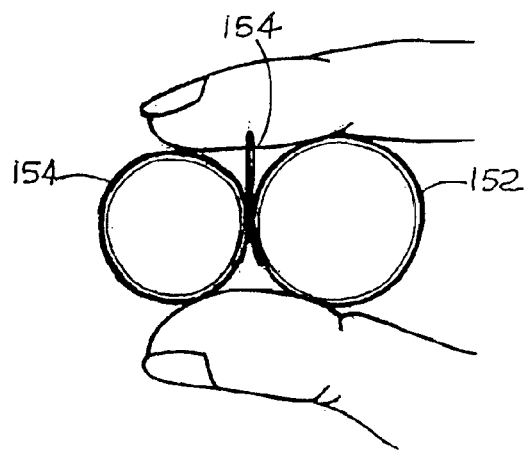
FIG. 13
FIG. 14
FIG. 16A
FIG. 15
FIG. 16B
FIG. 16C

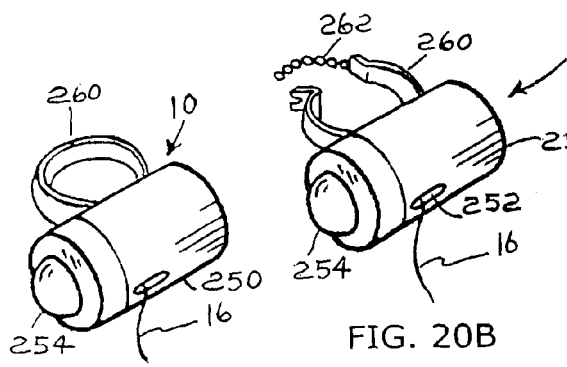
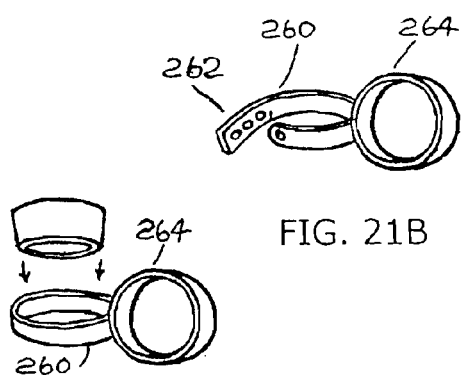
FIG. 20A  FIG. 20B  FIG. 21A  FIG. 21B
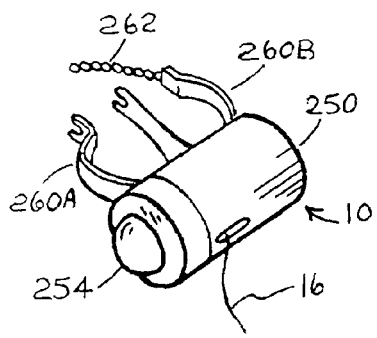
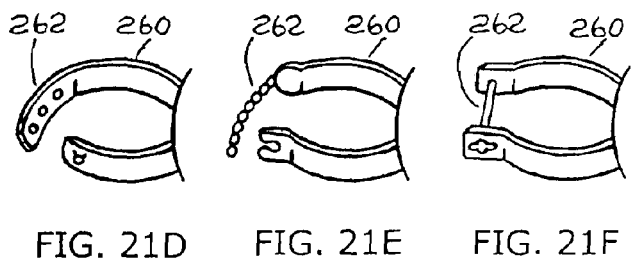
FIG. 20C  FIG. 21D  FIG. 21E  FIG. 21F
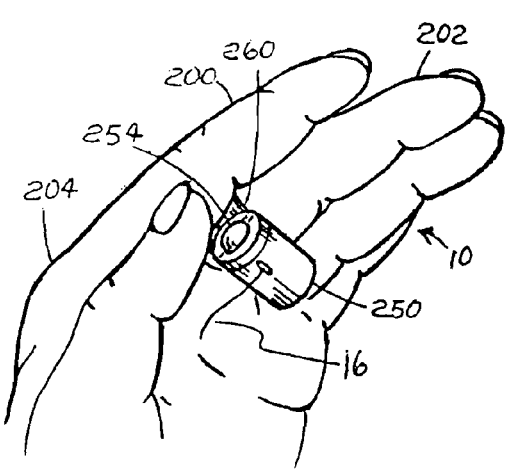
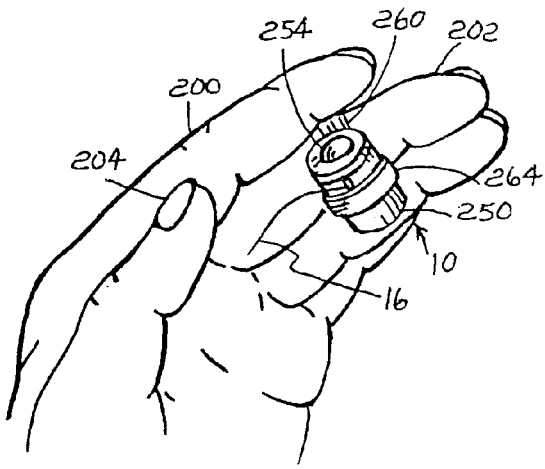
FIG. 20D  FIG. 21C

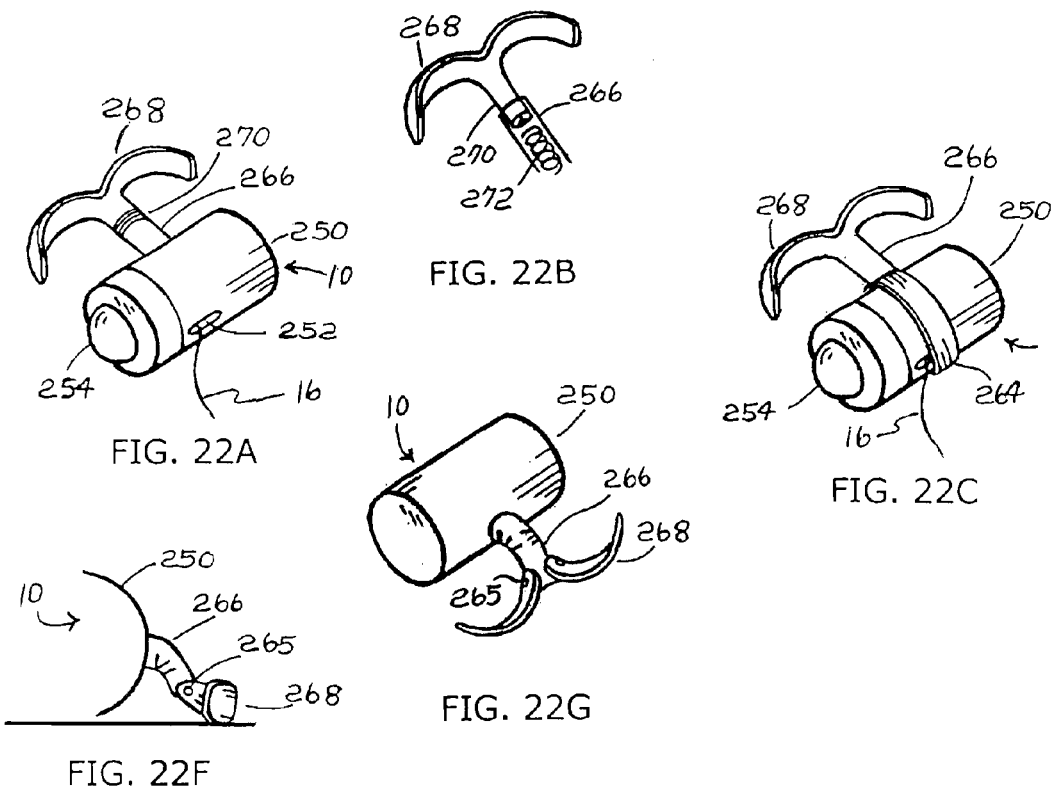
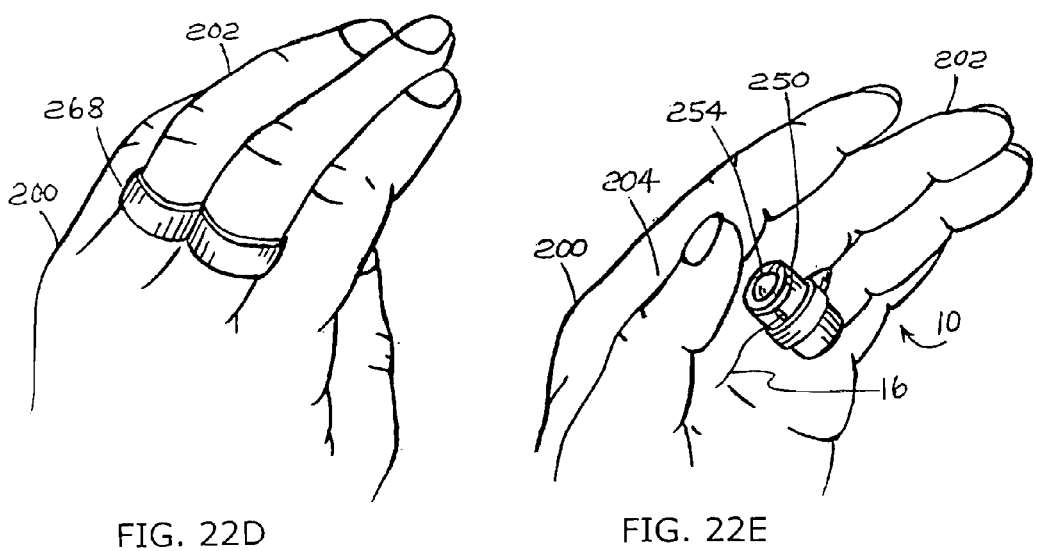
FIG. 22A
FIG. 22B
FIG. 22C
FIG. 22F
FIG. 22G
FIG. 22D
FIG. 22E

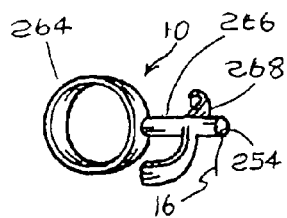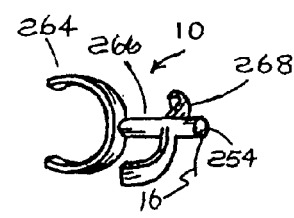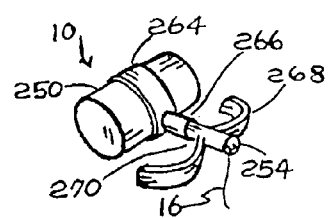
FIG. 23A  FIG. 23H  FIG. 23B
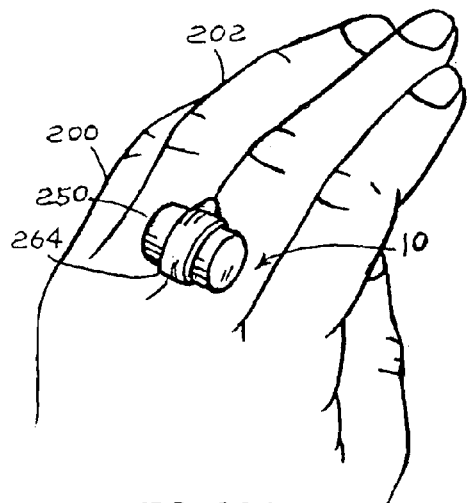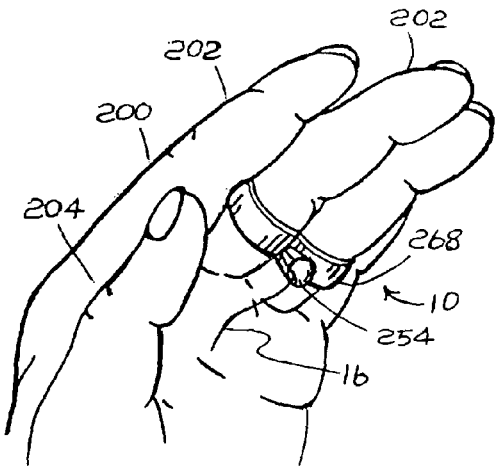
FIG. 23C  FIG. 23D
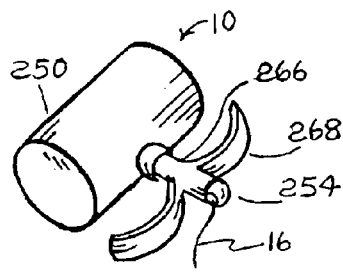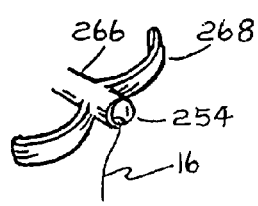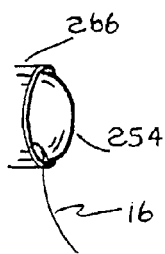
FIG. 23E  FIG. 23F  FIG. 23G

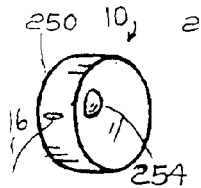 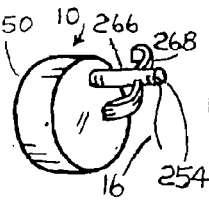 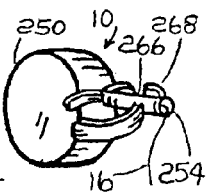 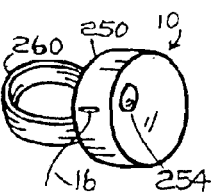 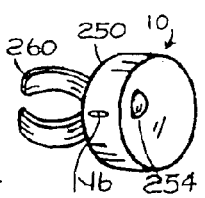
FIG. 25A  FIG. 25B  FIG. 25C  FIG. 25D  FIG. 25E
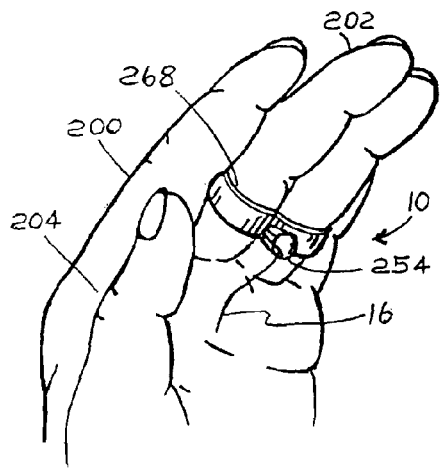 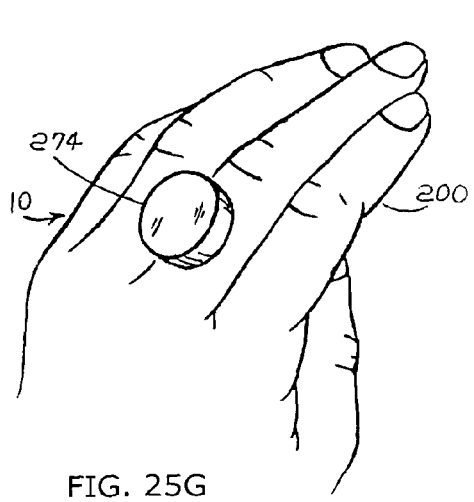
FIG. 25F  FIG. 25G
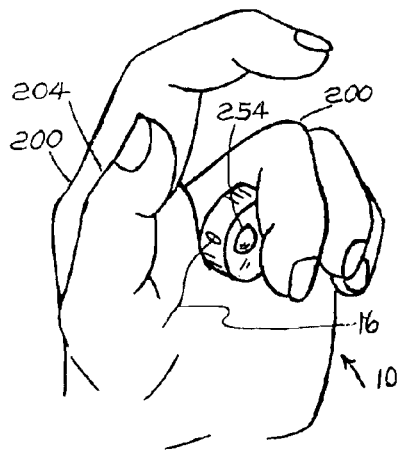 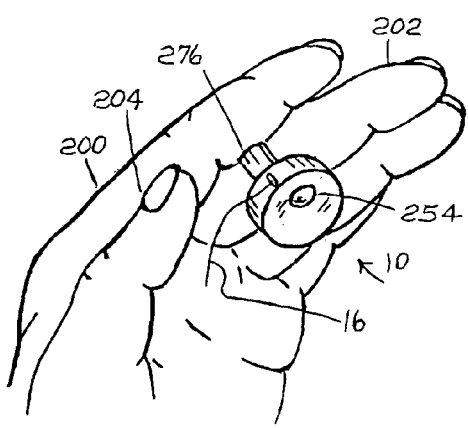
FIG. 25H  FIG. 25I

ORAL HYGIENE APPARATUSES

FIELD OF THE INVENTION

The present invention relates generally to dentistry. More particularly, the present patent discloses and protects plural apparatuses for enabling the practice of dental flossing to be carried out in a faster, more effective, convenient, and hygienic manner.

BACKGROUND OF THE INVENTION

Flossing has been recognized for more than a hundred years as an important aspect of dental hygiene. Nonetheless, at present in the United States, only about 65% of the population buys dental floss yearly and only 10-20% use it regularly. While most know they should floss, many do not for a number of reasons including the time, discomfort, and overall inconvenience involved. One knowledgeable in the art will be aware that numerous inventors have attempted to make flossing an easier, briefer, and neater operation. Unfortunately, even the combined prior art has failed to provide satisfactory solutions to the real problems at hand. Further contributing to the failure of the general population to floss properly and on a regular basis is a general lack of public awareness of the vital links between flossing and health and the importance of proper technique.

The consequences of not flossing are significant in terms of expense and the eventual inconvenience that far outweighs that represented by flossing. For example, it has been found that 75% of the public has gum problems. As a result, by the time the average person is 50, he or she has lost eight teeth. By sixty, ten to twelve teeth are likely lost while many will lose even more. This tooth loss commonly leads to costly and painful implants, bridges, and even full dentures whereby those suffering the tooth loss regret not being more diligent in their dental hygiene.

The need for proper dental hygiene has been emphasized still further by relatively recent scientific discoveries. By way of example, the Centers for Disease Control and Prevention (the CDC) has reported findings that provide overwhelming proof that infectious disease is commonly spread through touch, typically hand to mouth. Notably, the mouth is an ideal entry point for germs to invade the human body since, once germs have entered the mouth, the teeth and gums make perfect lodging points for permanent colonies of bacteria to develop. If not regularly removed or destroyed, such bacteria can incite continuing health problems throughout the body. As has been demonstrated by numerous studies including those conducted under the auspices of the National Institutes for Health (the NIH), oral bacterial infections can generate inflammation and contribute to many more widespread and serious maladies, including debilitating systemic illnesses such as cardiovascular, respiratory, and heart disease, diabetes, and even cancer, while accelerating the aging process itself.

Indeed, the importance of dental health has long been known to astute farmers, cowboys, and breeders who have appreciated that an experienced look into a horse's mouth will reveal volumes about the animal's overall health history and future. This valuable knowledge was eventually reflected in the "focal infection theory" of human disease: that local infections, especially oral abscesses and dental decay, rather than periodontal disease, could undermine the health of the whole body. As a result, widespread tooth extractions were commonplace until recent decades when improved dental techniques and antibiotics shifted the emphasis to saving teeth whenever possible.

However, with such discoveries as porphyromonas gingivalis bacteria in coronary artery blockages where they likely journeyed through tiny tears in diseased gum tissue, the focal infection theory has returned with the focus now on chronic periodontal disease. With that, some physicians now recommend antibiotics before dental work, particularly in patients with heart disease, since the poking and prodding inherent in dental work tends to nick the gums thereby unleashing potent pockets of germs directly into the bloodstream. Notably, similar adverse repercussions can be experienced during everyday tooth brushing and even chewing by those with bleeding gums as a result of, for example, gingivitis thereby leading to chronic systemic damage. Indeed, approximately forty diseases, including osteoporosis, obesity and elevated LDL cholesterol, have been decisively linked with periodontal infection.

With the knowledge provided by the CDC and others in relation to the critical role of touch in microbial transmission, new light has been shed on the need for proper dental hygiene, particularly flossing since it requires people to put their hands or other implements directly into their mouths for a prolonged, relatively invasive procedure thereby providing an optimal opportunity for the transfer of germs. Like carelessly performed minor surgery, improper flossing and flossing with non-sterile materials can cause harmful bacteria to be released directly into the bloodstream where they can cause havoc at distant sites. Accordingly, it will be appreciated that there is a need for the provision of sterile materials for enabling flossing in a safe and sterile manner.

Another major obstacle to proper, effective flossing is the failure of many to understand the health risks connected with poor dental hygiene. Many believe flossing is designed only to remove occasional food particles, and too few recognize the fundamental purpose of flossing, namely the removal of thin layers of bacteria-rich plaque that coat the sides of teeth above and below the gum line. Still further, even among those who realize the importance of plaque removal through flossing commonly practice flawed, inefficient methods for flossing. Some use only one very short piece of floss held between their thumbs and forefingers to complete their entire mouths while others use larger pieces improperly wrapped around their index fingers and not their middle fingers. Such improper flossing can lead to a "cross contamination" of bacteria from one tooth and gum area to another.

Proper flossing has the primary goal of removing as many bacteria as possible from each tooth and gum. As such, a clean section of floss should be used for each side of each tooth. To do so, the floss should be inserted between the teeth and gently moved just to the gum line. The floss can be made into a general U-shape around the tooth and carefully drawn away from gum line toward the biting surface of the tooth. The direction should not be reversed with the same section of floss since doing so would reintroduce the bacteria-laden plaque to the teeth. Therefore, the floss should be shifted laterally and the process repeated one or more times, each time using a fresh section. With the floss shifted laterally, the next section, such as the next inch, of floss should be moved under the gum line, around the tooth, and then carefully drawn from below the gums thereby removing deeply hidden plaque. The floss should not be sawn back and forth since doing so leaves most of the plaque in place and could damage the gums. Instead, the plaque-laden floss should be drawn in one direction only, namely away from the gum line. The same procedure should be repeated for each side of each tooth.

As the present discussion makes clear, proper flossing under prior art methods employing prior art devices is a time-consuming and messy operation that requires significant lengths of floss. For example, the typical person having no wisdom teeth will have 28 teeth in total thereby requiring a practical minimum of 56 inches of clean floss and a roughly equal amount of clean floss for their gums. With this, it becomes apparent that the 18 inches often recommended for the entire mouth is entirely inadequate. However, retaining and working with the significant lengths of floss needed for proper flossing can be problematic for a number of reasons. First, wrapping over 56 inches of floss around one's bare fingers inevitably leads to an uncomfortable and possibly dangerous constriction and loss of circulation in the user's fingers. Furthermore, by wrapping the floss repeatedly around his or her finger, the user tends to contaminate the dental floss before it can even enter his or her mouth. Still further, as the floss is moved laterally in the hope of providing a new section of floss, used, wet floss fully laden with contaminants must be wrapped around the finger or fingers on the user's opposite hand. Even further still, it must be noted that, particularly when wet, dental floss is hard to grip and otherwise maintain relative to a user's fingers thereby resulting in slippage, loss of grip, and less effective flossing. With these and further disadvantages in mind, it is clear that flossing with bare fingers can be a messy, unsanitary, unpleasant, and time-consuming activity whereby the disincentive against flossing is exaggerated.

In light of the foregoing, it will be appreciated that there is a true need for making the proper and consistent practice of dental flossing a reality for a significantly greater portion of the public. Accordingly, it will be further appreciated that there is a concomitant need for apparatuses and methods for rendering the flossing of one's teeth a faster, more convenient, effective, and hygienic endeavor such that more people will be willing to floss in a proper manner and on a regular basis.

SUMMARY OF THE INVENTION

Advantageously, the present invention is founded on the broadly stated object of making the proper and consistent practice of dental flossing a reality for a significantly greater portion of the public.

A resultant object of the invention is to improve not only the dental health of those taking advantage of the invention but also to improve the overall health of such persons by reducing or eliminating the occurrence and negative effects of dental decay, infections, and disease.

A more particular object of the invention is to provide dental hygiene apparatuses that render dental flossing faster, easier, more efficient, neater, and more hygienic.

A further object of particular embodiments of the invention is to provide a dental hygiene apparatus that easily and readily enables a user to employ a sterile, unused section of dental floss for each flossing maneuver.

Yet another object of the invention is to provide a dental hygiene apparatus that prevents contamination of unused portions of floss by used portions of floss and environmental sources of contamination.

Still another object of certain embodiments of the invention is to provide a dental hygiene apparatus that renders flossing a more comfortable practice by reducing or eliminating, among other things, the cutting off of circulation and the inadvertent slippage of floss during flossing.

These and further objects and advantages of the present invention will become obvious not only to one who reviews the present specification and drawings but also to one who has an opportunity to make use of an embodiment of the present invention. However, it will be appreciated that, although the accomplishment of each of the foregoing objects in a single embodiment of the invention may be possible and indeed preferred, not all embodiments will seek or need to accomplish each and every potential advantage. Nonetheless, all such embodiments should be considered within the scope of the present invention.

In carrying forth these objects, one embodiment of a dental hygiene apparatus according to the present invention comprises a dispensing member, a means for retaining dental floss relative to the dispensing member, an accumulating member, and a means for accumulating dental floss relative to the accumulating member. Under this arrangement, dental floss can be dispensed from the dispensing member and accumulated by the accumulating member thereby to enable a user to floss his or her teeth. Where necessary or desirable, the dispensing member and the accumulating member can be color coded.

In certain embodiments, the dispensing member and the accumulating member can each comprise a ring with an aperture for receiving a finger of a user. In any case, an activating switch can be operably associated with the means for retaining dental floss relative to the dispensing member for selectively enabling a dispensing of dental floss from the dispensing member. To prevent a refilling of the dispensing member, a means can be provided for preventing an accumulation of dental floss relative to the dispensing member including during a triggering of the activating switch. The activating switch can induce a dispensing of unlimited lengths of dental floss or a predetermined length of dental floss with each activation of the switch.

Furthermore, an activating switch can be operably associated with the means for accumulating dental floss relative to the accumulating member for selectively enabling a retraction of dental floss relative to the accumulating member. An accumulation of dental floss relative to the accumulating member during a triggering of the activating switch can be induced by any appropriate means including, by way of example, a coil spring, which can be rewindable. Furthermore, a means can be provided for preventing used dental floss from being retracted from the accumulating member even during a triggering of the activating switch.

Dental floss can be retained relative to the dispensing member and the accumulating member by a bobbin that can be disposed within a housing. Dental floss can be dispensed and accumulated through respective apertures in the dispensing and accumulating members. Furthermore, a scrubber element, which can be removable and replaceable, can be retained relative to the accumulating member adjacent to the aperture for clearing debris from the dental floss.

To accommodate users with different finger sizes, the dental hygiene apparatus can include a means for varying the sizes of the apertures in the dispensing ring and the accumulating ring. The means for varying the sizes of the apertures can vary within the scope of the invention including, by way of example, removable sizing members for being removed from the apertures and inserts for being inserted into the apertures. In particular embodiments, means can be provided for enabling a removal and replacement of the bobbins relative to the housings of the accumulating and dispensing members.

In other embodiments, the dental hygiene apparatus can comprise only a dispensing member or only an accumulating member, each being considered a floss retaining member. The floss retaining member can have a means for retaining dental floss and a means for enabling a transfer of dental floss relative to the floss retaining member, which can comprise an accumulation or a dispensing of dental floss. A means for retaining the floss retaining member relative to a hand of a user can be provided and can comprise, by way of example, a ring member coupled to the floss retaining member for receiving a finger of the user. The ring can be adjustable in circumference by any one of a number of different means. In certain constructions, there can be first and second rings coupled to the floss retaining member for retaining it relative to a user's hand. The floss retaining member can alternatively be retained by a user by a band for surrounding, by way of example, a user's hand, wrist, multiple fingers, or any other portion of the user. The band can be adjustable in circumference by any suitable means.

Alternatively, the means for retaining the floss retaining member relative to the hand of the user can take the form of an opposed hook arrangement coupled to the floss retaining member by a post. The effective length of the post can be extensible and retractable by any suitable means. Where a post is provided, dental floss can be transferred, whether by being dispensed or retracted, from adjacent to the distal end of the post. Under such an arrangement, the post can traverse between a user's fingers to transfer dental floss. In such a case, an activating trigger can be disposed adjacent to the distal end of the post.

The floss retaining member can have a floss retaining shell with a bobbin rotatably retained relative thereto. An aperture in the shell can enable dental floss to pass therethrough. In certain embodiments, the floss retaining shell can be barrel-shaped, and an activating trigger can be disposed at a first end of the floss retaining shell. In other embodiments, the floss retaining shell can have a rounded body shape, such as an egg or spherical shape.

The floss retaining member can comprise a ring with an aperture for receiving a finger of a user and a means, such as a rotatable bobbin, for retaining dental floss within the ring. In certain embodiments, the floss retaining member can further include a second ring coupled to the first ring whereby the floss retaining member will take the form of floss retaining knuckles. In such a case, individual bobbins can be retained in each of the rings. Alternatively, a single bobbin can span both rings surrounding both apertures.

In any event, the dental hygiene apparatus can additionally include a finger shield arrangement for improving the ability of the user to floss in a sanitary manner. The finger shield can comprise a tubular member for receiving a finger of a user in a mating relationship. The tubular member can be retained relative to a finger of a user by a means, such as an adhesive tab, for constricting the same. In certain embodiments, a second tubular member can be separably coupled to the tubular member, such as by a first adhesive tab fixed to the tubular member and a second adhesive tab fixed to the second tubular member. Under such a construction, the first and second adhesive tabs can be separated to separated the tubular members, and the tubular members can be retained relative to a user's fingers by a constricting of the same using the adhesive tabs.

Of course, one should remain mindful that the foregoing discussion is designed merely to outline broadly the more important features of the invention to enable a better understanding of the detailed description that follows and to instill a better appreciation of the inventor's contribution to the art. Before an embodiment of the invention is explained in detail, it must be made clear that the following details of construction, descriptions of geometry, and illustrations of inventive concepts are mere examples of possible manifestations of the invention.

BRIEF DESCRIPTION OF THE DRAWINGS

In the accompanying drawings:

FIGS. 3A through 3G depict views of different embodiments of the dispensing ring, the accumulating ring, and the bobbin;

FIG. 13 is a view in front elevation of a finger shield arrangement according to an alternative embodiment of the invention;

FIG. 14 is a view in front elevation of an alternative finger shield arrangement;

FIG. 15 is a perspective view of a further refinement of the finger shield arrangement;

FIGS. 16A through 16C depict steps in opening the finger shields for use;

FIGS. 20A through 20D are perspective views of a finger-engaging embodiment of the automated flossing system;

FIGS. 21A through 21F are perspective views of further means and methods for retaining an accumulating/dispensing arrangement under the present invention;

FIGS. 22A through 22G are perspective views of still further means and methods for retaining an accumulating/dispensing arrangement;

FIGS. 23A through 23H are perspective views of alternative constructions for disposing and retaining the accumulating/dispensing arrangement;

FIGS. 25A through 25I are perspective views of still further embodiments of accumulating/dispensing arrangements;

DETAILED DESCRIPTION OF PREFERRED EMBODIMENTS

As is the case with many inventions, the present invention for dental hygiene apparatuses is subject to a wide variety of embodiments. However, to ensure that one skilled in the art will fully understand and, in appropriate cases, be able to practice the present invention, certain preferred embodiments of the broader invention revealed herein are described below and shown in the accompanying drawings.

Figure 1:
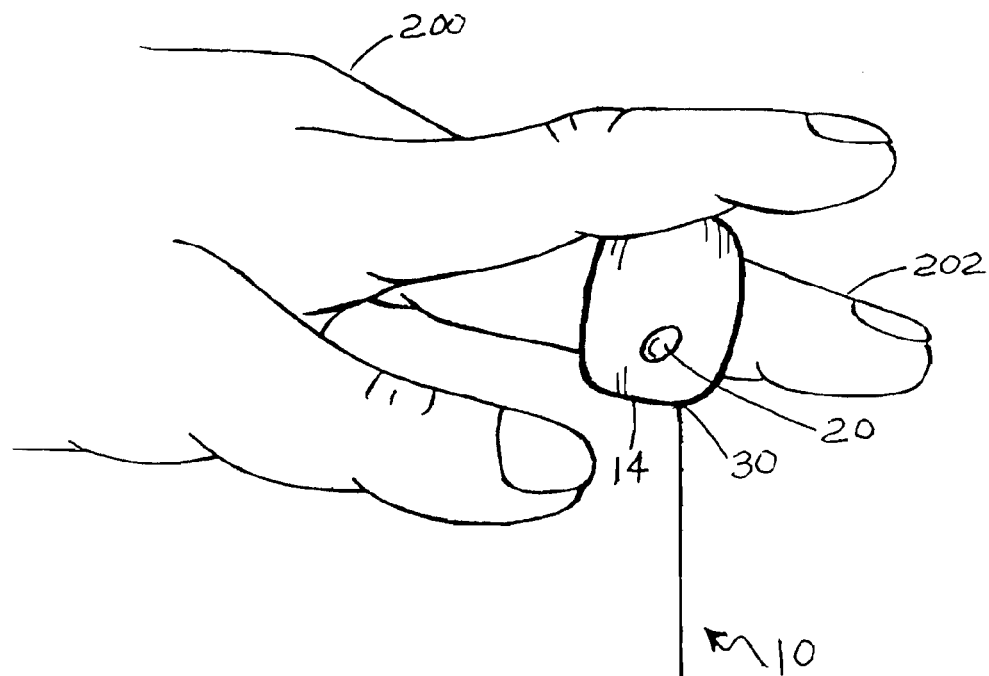
FIG. 1 is a perspective view of an automated flossing system according to the present invention shown in use.
Figure 1:
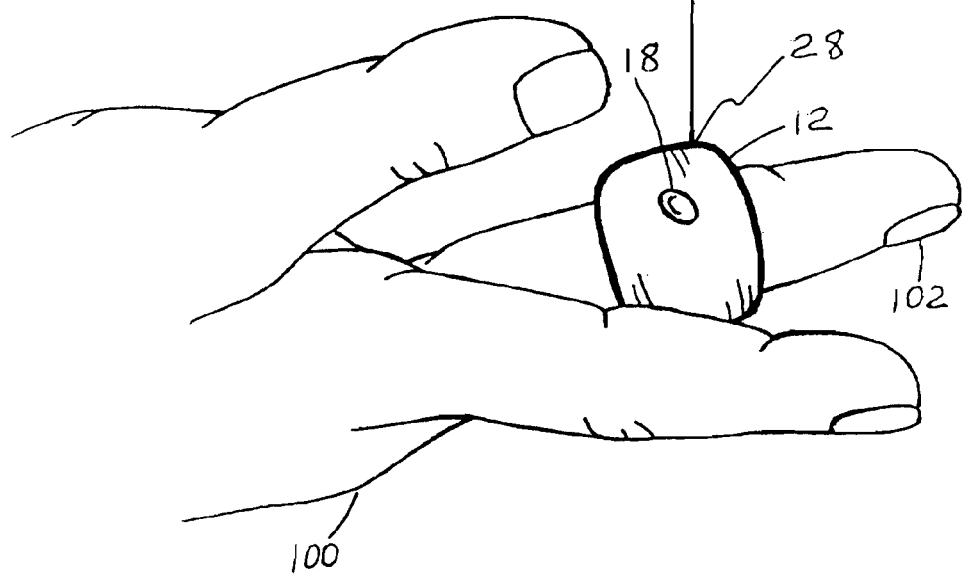

With this in mind and looking more particularly to the accompanying figures, a first preferred embodiment of a dental hygiene apparatus is indicated generally at 10 in FIG. 1. There, one sees that the dental hygiene apparatus 10 in this embodiment comprises a dispensing ring 12 that feeds dental floss 16 to a second, accumulating ring 14. Together, the dispensing ring 12 and the accumulating ring 14 form an automated flossing system, which is also indicated at 10. In FIG. 1, the automated flossing system 10 is shown as it might be employed during flossing. As such, the dispensing ring 12 is retained on the middle finger 102 of, in this example, the user's left hand 100 and the accumulating ring 14 is retained on, in this example, the middle finger 202 user's right hand 200.

As will be detailed herein and as one can perceive from FIGS. 1, 2A, 2B, and 2C, the dispensing ring 12 retains and selectively dispenses sterile, unused dental floss 16 through an aperture 28 while the accumulating ring 14 selectively receives and retains used dental floss 16 through an aperture 30. In this exemplary embodiment, the dispensing ring 12 has an activating switch 18 for selectively allowing floss 16 to be withdrawn therefrom and for preventing the inadvertent withdrawal of floss 16. Under one arrangement, for example, the activating switch 18 can be pressed to allow floss 16 to be retracted and released to lock the floss 16 against being dispensed. Similarly, the accumulating ring 14 has an activating switch 20 that, when pressed, causes floss 16 to be retracted into the accumulating ring 14 and, when released, prevents retracted floss 16 from being pulled from within the accumulating ring 14.

The dispensing ring 12 and the accumulating ring 14 can be spring wound, such as by means of a coil spring (not shown in these figures), such that each will tend to draw floss 16 into itself. Alternatively, floss 16 can be drawn into the dispensing ring 12 and the accumulating ring 14 by, for example, the action of the user's pressing of the activating switch 18 or 20. With regard to the dispensing ring 12 when spring force is used for biasing floss 16 toward a retracted condition, the spring force can be overcome to allow floss 16 to be dispensed. However, since the accumulating ring 14 will retain contaminated used floss 16, it can preferably lock floss 16 from being dispensed even when the activating switch 20 is pressed. The amount of floss 16 that is retracted or released when the activating switches 18 and 20 are pressed can be infinitely variable such that as little or as much floss 16 can be extended or retracted as the user might desire. Alternatively, the amount of floss 16 can be predetermined such that a given amount, such as from 1 inch to 6 inches, can be allowed to be released or retracted with each pressing of the activating switch 18 or 20.

Of course, since the dispensing ring 12 is intended to retain sterile floss 16 only and to be disposed of when the pre-loaded floss 16 is exhausted, the preferred dispensing ring 12 may incorporate a means for allowing floss 16 to be drawn from the dispensing ring 12 and for preventing it from being drawn into the dispensing ring 12. This could be done in a plurality of ways. Under one arrangement, that means could comprise a means for ensuring a unidirectional rotation of the bobbin 38 that could be embodied in a ratchet arrangement between the bobbin 38 and the torroidal housing 15 such that the user could activate the switch 18 to allow a dispensing rotation of the bobbin 38 but not a retraction of floss 16. The floss 16 could be pulled from within the housing 15, possibly by overcoming the force of a coil spring 32 as is shown, for example, in FIGS. 3A through 3G.

Alternatively, the coil spring 32 could be eliminated, and floss could simply be pulled from the torroidal housing 15 when the switch 18 is activated. In such a case, a ratchet arrangement could again be employed for preventing any retraction of floss 16. Alternatively, a drag arrangement between the bobbin 38 and the housing 15 could prevent counter-rotation of the bobbin 38. Still further, a lack of counter-rotation of the bobbin 38 could be ensured simply by shielding it within the torroidal housing 15 with no means for producing a winding rotation.

In preferred embodiments, the dispensing ring 12 and the accumulating ring 14 can be color coded to enable the user to distinguish between them most readily. For example, the dispensing ring 12 could be colored blue thereby indicating to the user the sterile nature of the retained floss 16 while the accumulating ring 14 could be colored yellow thereby providing an indication of the contaminated nature of the used floss 16 retained therein.

Figure 2A:
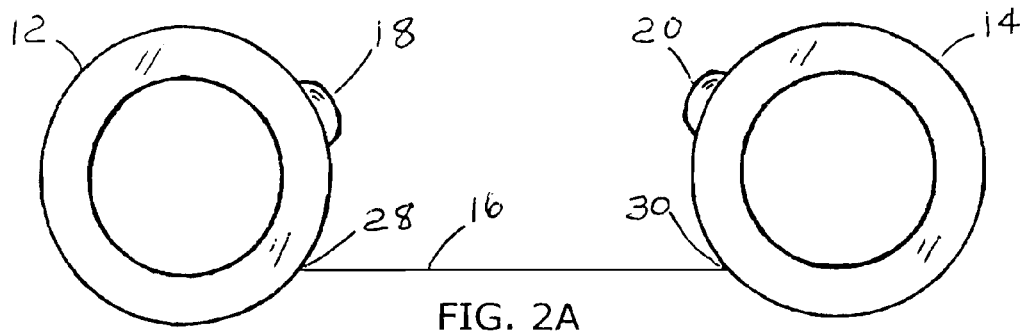
FIGS. 2A through 2C comprise views in side elevation of constructions of the automated flossing system under the present invention.
Figure 2B:
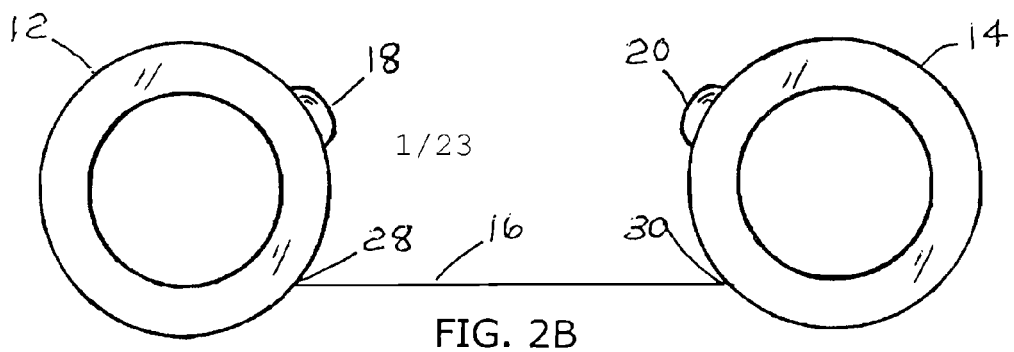
Figure 2C:
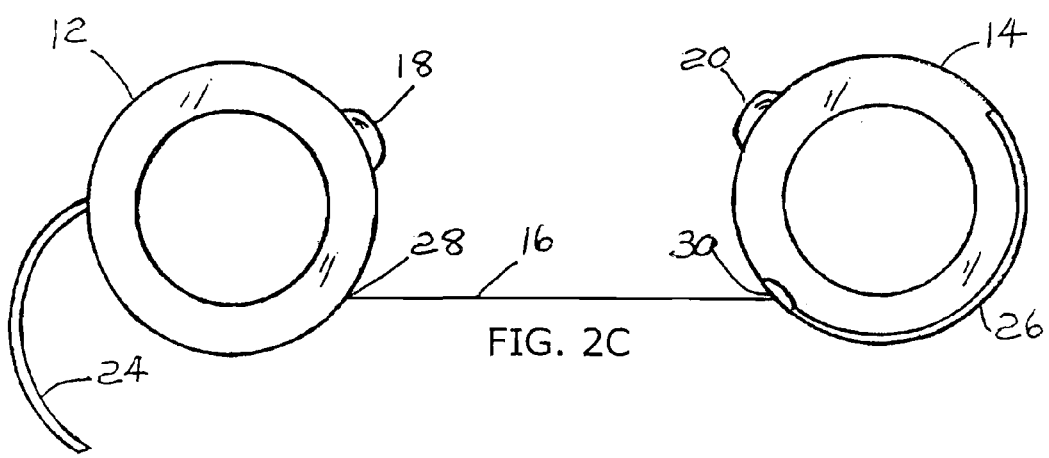

An alternative embodiment of the automated flossing system 10 is shown in FIG. 2C. There, the automated flossing system 10 again includes a dispensing ring 12 that retains and dispenses sterile floss 16 and an accumulating ring 14 that retains used floss 16. However, in this embodiment, the accumulating ring 14 has a foam scrubber 22 disposed adjacent to or within the aperture 30 that leads to the inner volume of the accumulating ring 14 for clearing larger elements of removed debris from the used floss 16 before it enters the accumulating ring 14. Also, in the embodiment of FIG. 2C, the dispensing ring 12 and the accumulating ring 14 each have access panels 24 and 26 that can be opened to allow access to the retained floss 16 so that, among other things, any breakage or knotting of the floss 16 can be remedied. In this exemplary embodiment, the access panels 24 and 26 can be formed unitarily with the dispensing ring 12 and the accumulating ring 14 and can be pivotably retained by a living hinge or any other appropriate mechanism.

FIGS. 3A through 3D show one possible arrangement for enabling the accumulating ring 14 to retract floss 16 automatically with a pressing of the activating switch 20. With combined reference to FIGS. 3A and 3B, one sees that a coil spring 32 is retained relative to the torroidal housing 15 of the accumulating ring 14. More particularly, the coil spring 32 has a first end fixed to an inner annular wall of the torroidal housing 15 and a second end comprising a locking tab 36. The torroidal housing 15 has a corresponding locking tab 34 disposed on an outer annular wall thereof for engaging the locking tab 36 of the coil spring 32 thereby preventing the coil spring 32 from becoming inadvertently unwound. The activating switch 20 itself is biased radially outward to a non-activated position wherein the locking tabs 34 and 36 are fully engaged.

The second, outer end of the coil spring 32 is drivably coupled to a bobbin 38 that is rotatably retained within the torroidal housing 15 of the accumulating ring 14. Of course, the drivable coupling between the bobbin 38 and the coil spring 32 could be accomplished in a plurality of ways that would readily occur to one skilled in the art. In this exemplary embodiment, the coil spring 32 and the bobbin 38 are disposed laterally to one another and the coupling is carried out by a drive dowel 42 that fixes the bobbin 38 for rotation with the second end of the coil spring 32. Of course, the bobbin 38 and the coil spring 32 could be coupled in any one of a plurality of alternative keying mechanisms. For example, the keying could be carried out by providing a geared or notched edge on the bobbin 38 in combination with an engaging geared or notched edge fixed to the coil spring 32. Under the arrangement of FIG. 3B, the user can depress the activating switch 20 to disengage the locking tabs 34 and 36. With this, the force of the wound coil spring 32 will tend to cause it to unwind. As the coil spring 32 unwinds, it will rotate the bobbin 38 thereby winding additional used dental floss 16 onto the bobbin 38.

Figure 3E:
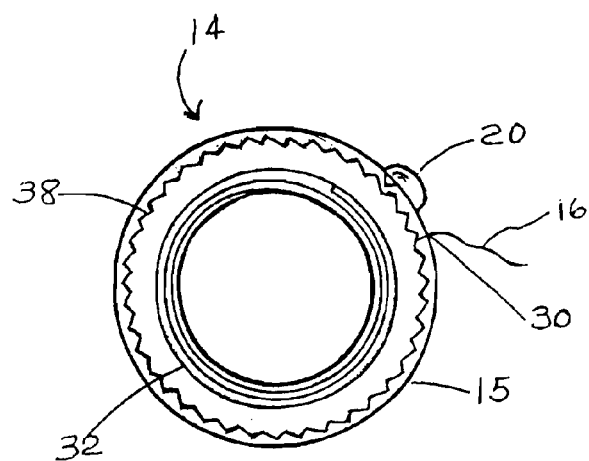

Of course, other arrangements are well within the scope of the invention. For example, FIG. 3E depicts an arrangement for the accumulating ring 15 wherein the coil spring 32 is disposed radially inward of the bobbin 38 within the torroidal housing 15. More particularly, the bobbin 38 is rotatably disposed within the torroidal housing 15 with the activating switch 20 selectively locking it against rotation. The coil spring 32 is disposed in an annular open space between the inner wall of the bobbin 38 and the inner wall of the torroidal housing 15. A first end of the coil spring 32 is fixed to the inner wall of the torroidal housing 15 while a second end of the coil spring 32 is fixed to the inner wall of the bobbin 38. In this case, the activating switch 32 has a locking tooth thereon that is selectively engaged with locking teeth on the bobbin 38. With this, when the activating switch 20 is activated, such as by being tilted or slid away from the bobbin 38, the switch 32 will disengage from the teeth on the bobbin 38 thereby allowing it to rotate, and the force of the spring 32 will induce that rotation thereby winding in a length of used dental floss 16.

Still further, it will be appreciated that, where the rotation of the bobbin 38 is induced by the spring force, the coil spring 32 may become unwound or fully wound and therefore ineffective before the usefulness of the dispensing ring 12 or the accumulating ring 14 has expired. For example, with regard to the dispensing ring 12 where a user might draw floss 16 from the dispensing ring 12 by overcoming the force of the coil spring 32, the coil spring 32 might become fully wound such that no further floss 16 can be withdrawn. With regard to the accumulating ring 14 where contaminated floss 16 is to be pulled into the accumulating ring 14 by the unwinding force of the coil spring 32, the coil spring 32 can become fully unwound such that no further floss 16 can be reeled into the accumulating ring 14.

Figure 3F:
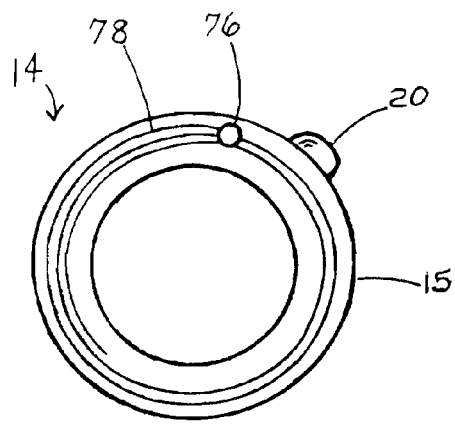
Figure 3G:
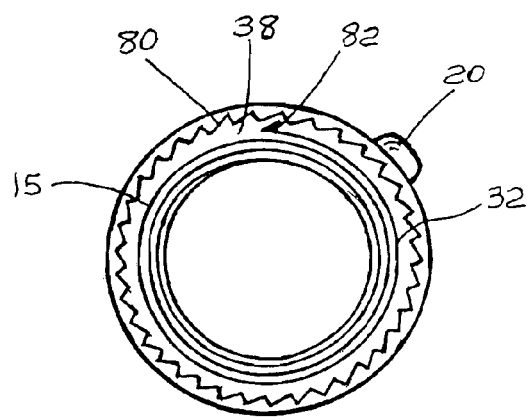

Advantageously, in certain embodiments, the present invention can incorporate a means for enabling the repositioning of an end of the coil spring 32 such that the user can rewind or unwind the coil spring 32 to restore the winding ability of the dispensing ring 12 and the accumulating ring 14. Although many such means would be within the scope of the invention, one possible means is shown in FIGS. 3F and 3G. There, an end, which can be either the first end or the second end, of the coil spring 32 is repositionable about the annular peripheral wall of the torroidal housing 15 by means of a ratchet and pawl relationship while the opposite end of the coil spring 32 is drivably associated with the bobbin 38. More particularly, the outer annular wall of the torroidal housing 15 has a plurality of inclined teeth therealong such that it forms a ratchet surface 80 while the end of the coil spring 32 has a pawl 82 fixed thereto. A winding handle 76 that is coupled to the pawl 82 end of the coil spring 32 is disposed exterior to the torroidal housing 15 and can travel along an annular channel 78. Under this arrangement, when the coil spring 32 has become fully wound or unwound, the user can replenish the force in the coil spring 32 simply by employing the winding handle 76 to disengage the pawl 82 from the ratchet surface 80 if necessary and then sliding the winding handle 76 along the annular channel 78 thereby to wind or unwind the coil spring 32 as the need may be.

As can be seen best in FIG. 3C, the bobbin 38 can have one or a plurality of wedge slots 64 cut or formed into one or both of its radial walls 66. Advantageously, in combination with, for example, the access panel 26, the user will be able to reattach or attach floss 16 as necessary in a convenient manner. For example, if a strand of floss 16 were to break during use of the automated flossing system 10, the user need only open the access panel 26 and wedge the loose end of the floss 16 into the wedge slot 64 whereby the accumulating ring 14 will be ready for drawing in more floss 16 as necessary.

It should be appreciated that much of the structure disclosed relative to the accumulating ring 14 is incorporated to equal advantage relative to the dispensing ring 12. However, with the primary function of the dispensing ring 12 being essentially opposite to that of the accumulating ring 14, certain elements could be oppositely arranged. For example, the coil spring 32 could be arranged to propel dental floss 16 from the torroidal housing 15 by exerting an unwinding force on the bobbin 38. Alternatively, the bobbin 38, the coil spring 32, and the associated components could be arranged such that a pressing of the activating switch 18 will again allow the bobbin 38 to rotate in a manner that would tend to reel dental floss 16 but that allows the force of the coil spring 32 to be overcome to allow an unwinding of floss 16.

Figure 4:
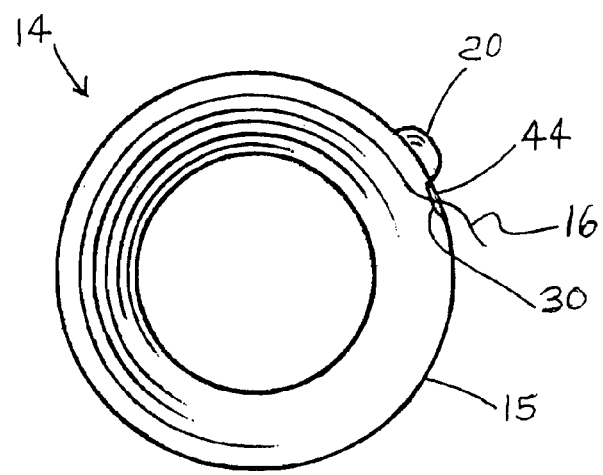
FIG. 4 is a view in side elevation of an alternative embodiment of the accumulating ring.

Another possible arrangement is shown in FIG. 4. There, the accumulating ring 14 is again founded on a torroidal housing 15 for retaining a length of used dental floss 16, and an activating switch 20 is again provided for allowing a reeling in of used floss 16. However, in this case, the activating switch 20 is a simple frictional switch that is slidably associated with the outer annular wall of the torroidal housing 15 for selectively sealing off the aperture 30 and thereby frictionally fixing the floss 16 against movement by compressing it between the activating switch 20 and the torroidal housing 15. To ensure a positive frictional engagement, at least one but preferably both of the activating switch 20 and the torroidal housing 15 will have locking teeth 44 disposed thereon.

Figure 5A:
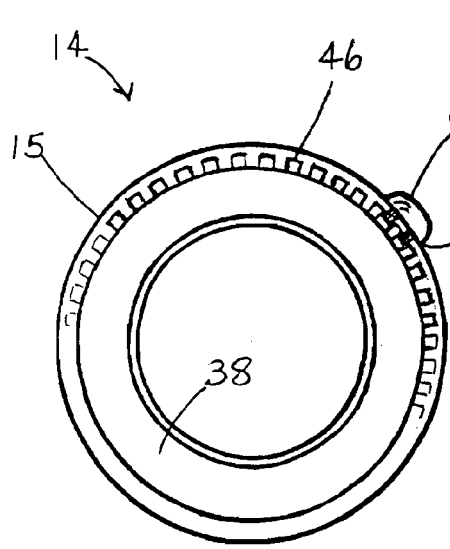
FIGS. 5A and 5B comprise views in side and front elevation of still further embodiments of the accumulating ring.

In FIG. 5A, the bobbin 38 has a plurality of locking teeth 46 projected radially from along its circumference. The activating switch 20 has one or more corresponding locking teeth 48 for selectively engaging the locking teeth 46 on the bobbin 38 thereby to fix the bobbin 38 against inadvertent rotation.

Figure 5B:
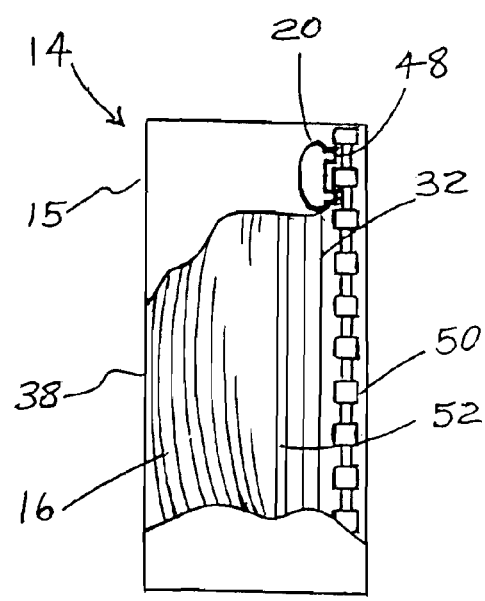

In FIG. 5B, an annular wall 52 sized to fit just within the torroidal housing 15 bifurcates the bobbin 38 into a first axial component for retaining the dental floss 16 and a second axial component for retaining the coil spring 32, which can have a first end fixed to the bobbin 38 and a second end fixed relative to the torroidal housing 15. The activating switch 20 again can operate under any appropriate arrangement. In the illustrative embodiment of FIG. 5B, the activating switch 20 has one or more locking teeth 48 disposed thereon and the bobbin 38 has a plurality of locking teeth 50 projecting therefrom for selectively engaging the locking teeth 48 on the activating switch 20 to fix the bobbin 38 against rotation. Of course, numerous alternative arrangements are possible. For example, one or more dowels or other keying mechanisms can be employed for interengaging the bobbin 38 with the torroidal housing 15.

Figure 6A:
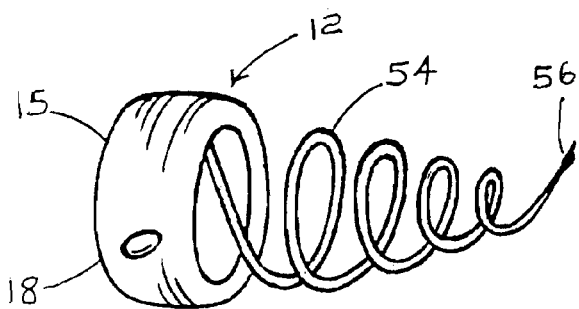
FIGS. 6A through 6C comprise views of still another embodiment of the dispensing ring including a sizing arrangement.
Figure 6B:
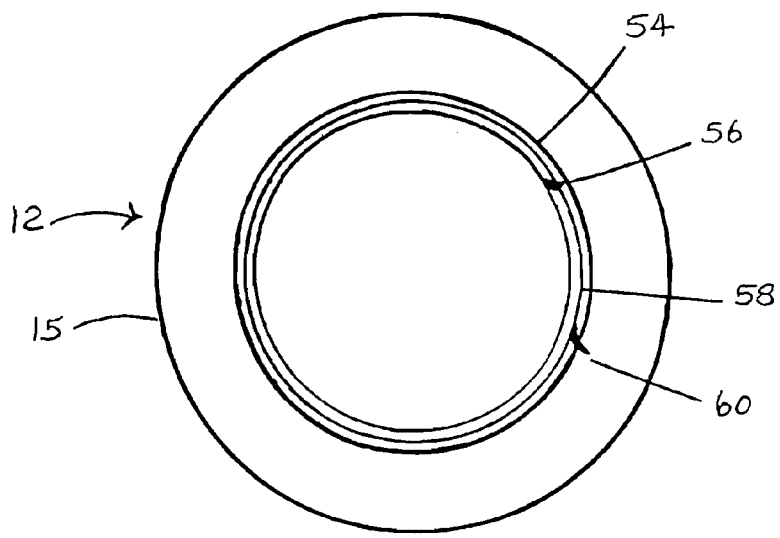
Figure 6C:
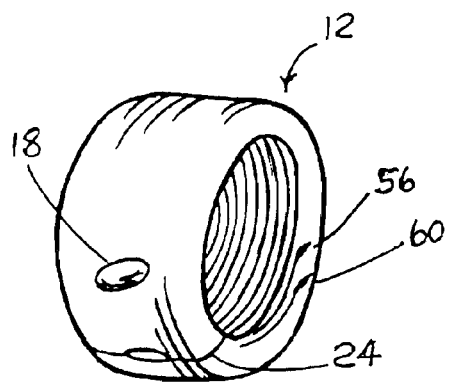

Since the dispensing ring 12 and the accumulating ring 14 are to be worn as rings, it may be preferable for the automated flossing system 10 to be sized or sizable to accommodate wearers with different finger sizes. Of course, this could be achieved simply by molding or otherwise forming the torroidal housing 15 of each of the dispensing ring 12 and the accumulating ring 14 with differently sized inner annular openings or finger holes. However, for a number of reasons, it may be preferable to form the torroidal housings 15 and other components of the dispensing ring 12 and the accumulating ring 14 with uniform dimensions and to adapt these fixed arrangements to user's with different finger sizes. While a number of sizing means would readily occur to one skilled in the art, a first preferred means is depicted in FIGS. 6A through 6C relative to the dispensing ring 12 with it being expressly noted that the same methods and structures could be employed relative to the accumulating ring 14. There, the inner annular wall of the torroidal housing 15 is lined with one or more layers of a removable sizing member 54. In this case, the sizing member 54 comprises a spirally wound strip, which is also indicated at 54, that terminates in a pull tab 56.

Under this arrangement, the dispensing ring 12 will have a given, smallest ring size upon initial manufacture. If that ring size is appropriate for the user, then the dispensing ring 12 can simply be put to use. If the ring size is too small, however, the user can pull on the tab 56 thereby to unwind and remove the spirally wound sizing member 54 thereby creating a larger ring size. As FIG. 6B shows, there can be multiple sizing members 54 and 58, each with a pull tab 56 or 60, for making further ring sizes available to the user.

Figure 7A:
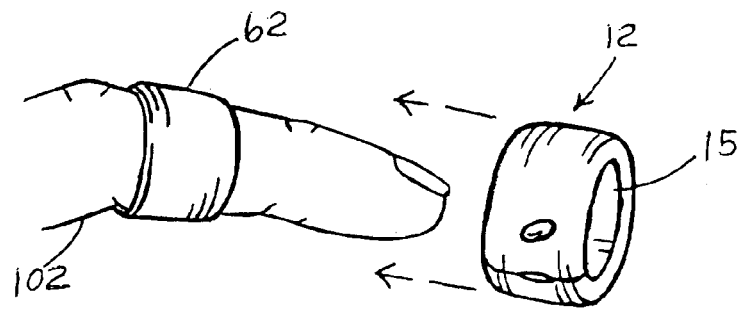
FIGS. 7A through 7C depict a further sizing arrangement under the present invention.
Figure 7B:
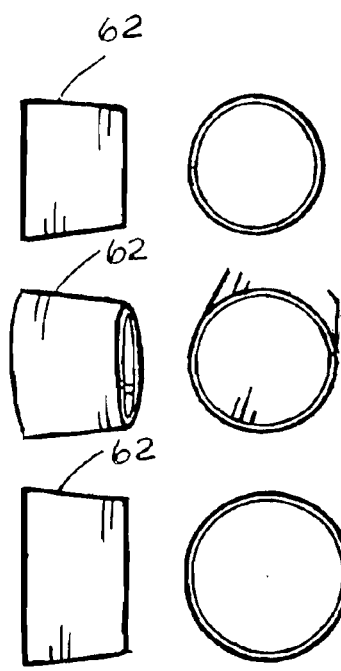
Figure 7C:
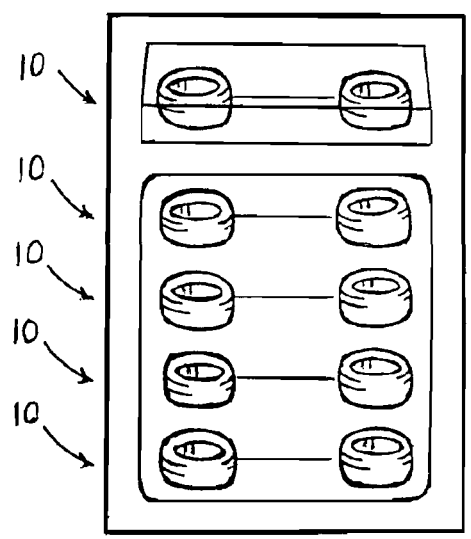

Alternatively, as is shown in FIGS. 7A and 7B, the effective size of the annular opening in the torroidal housings 15 could be adjusted by use of variably sized inserts 62. The inserts 62 can have a universal outer diameter for frictionally or otherwise engaging the inner wall of the torroidal housing 15 but a particularly sized inner diameter for engaging the particular user's finger. In certain embodiments, the torroidal housings 15 can be crafted with generalized sizes, such as small, medium, and large, and those generalized sizes can be particularized by use of variably sized inserts 62 for each generalized size. Under such a construction, the size gap between, for example, medium and large generalized sizes can be bridged with one or more particularly sized inserts 62. As FIG. 7B shows, the inserts 62 could have a tapered outside diameter for better enabling them to be slipped into the torroidal housings 15. With this, a single automated flossing system 10 could be adapted for and used by users with different hand sizes. Indeed, such an arrangement would enable different persons, such as family members, to have individual inserts 62 that could be used to make a single set or size category of dispensing and accumulating rings 12 and 14 mutually usable. FIG. 7C shows a set of automated flossing systems 10 as they might be packaged for sale.

Figure 8:
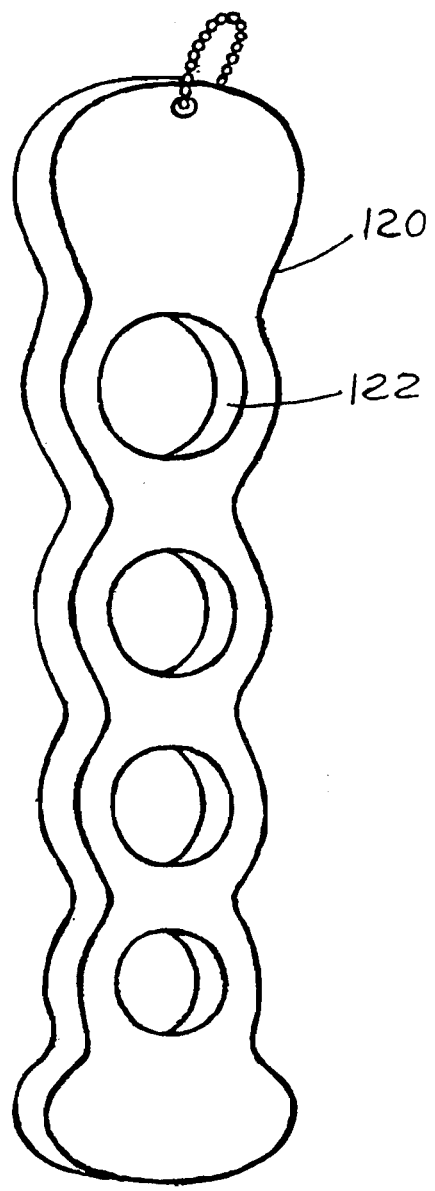
FIG. 8 is a perspective view of a sizing gauge under the present invention.
Figure 9:
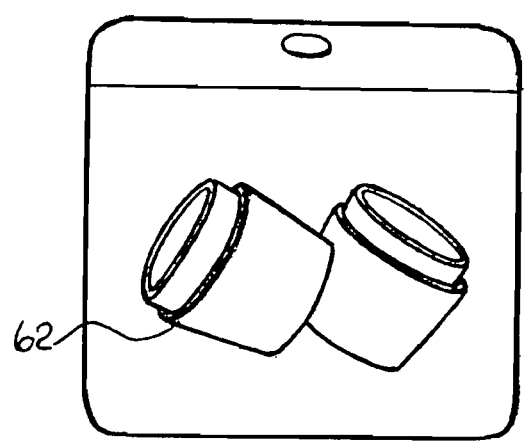
FIG. 9 depicts a packaging arrangement for sizing inserts according to the present invention.

To assist users in determining the appropriately sized automated flossing system 10, a guide can be provided at the point of purchase. For example, as is shown in FIG. 8, an insert gauge 120 with a plurality of sizing apertures 122 can be securely retained at the point of sale. Also, as FIG. 9 shows, inserts 62 can be separately packaged and sold. With this, a user can determine his or her most suitably sized automated flossing system 10 and whether any inserts 62 will be required so that the users finger size can be accommodated most comfortably and accurately.

Figure 10A:
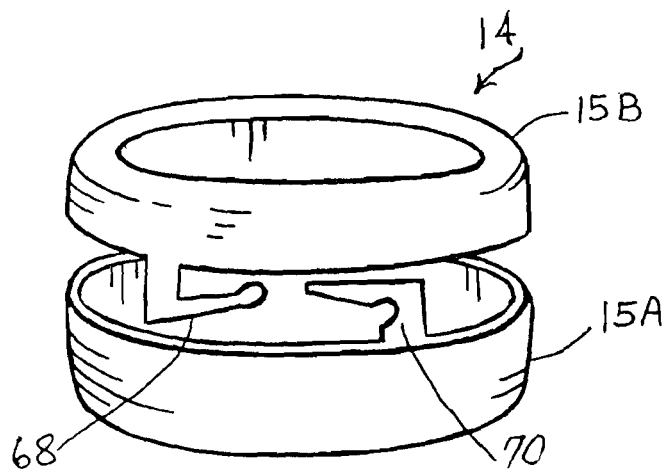
FIGS. 10A through 10C illustrate one potential arrangement for the dispensing ring.
Figure 10B:
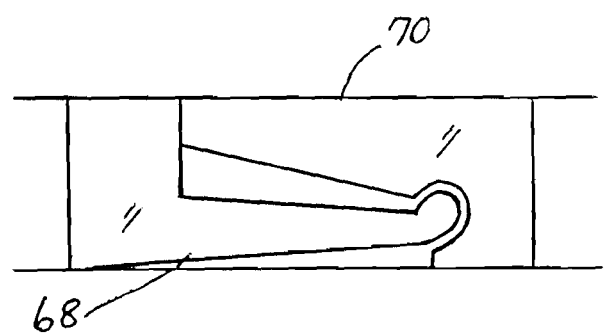
Figure 10C:
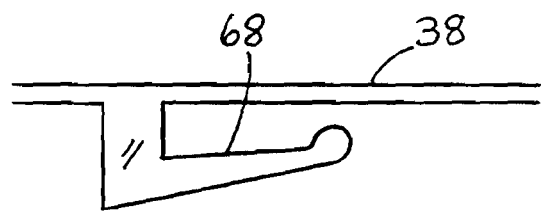

In a still further refinement of the invention, there may be included a means for removing and replacing full or partially filled bobbins 38 relative to accumulator rings 14. Such a means advantageously could provide room for the retention of further lengths of used dental floss 16. Just as advantageously, such a means would enable a user to dispose of fouled dental floss 16 as necessary or desirable thereby preventing any adverse repercussions resulting from the presence of odorous, decaying, or otherwise objectionable used floss 16. This too could be carried out in a plurality of ways under the present invention. One possible arrangement is shown in FIGS. 10A through 10C. There, a disposable bobbin 38 (not shown) can be removably and replaceably received between a first torroidal housing half 15A and a second torroidal housing half 15B. The first and second torroidal housing halves 15A and 15B will preferably be readily separated but securely joined to enable the secure yet accessible retention of disposable bobbins 38. In the illustrative embodiment, the first and second torroidal housing halves 15A and 15B are joined by mutually engaging first and second locking arms 68 and 70 that extend from the first and second torroidal housing halves 15A and 15B respectively. To enable the strand of floss 16 to be severed most conveniently, the second locking arm 70 could incorporate or be formed with a sharp edge, possibly a blade of metal. The bobbin 38 again can have one or more wedge slots 64 incorporated therein.

Under such a construction, a bobbin 38 full or partially full with soiled dental floss 16 can be removed and discarded simply by the users separating the first and second torroidal housing halves 15A and 15B, withdrawing the bobbin 38 from, for example, the first torroidal housing half 15A, and cutting the floss 16 with the sharp edge of the second locking arm 70. An end of a sterile length of floss 16 can then be wedged into the wedge slot 64, and the floss 16 can be wrapped around the bobbin 38 as necessary. The new bobbin 28 can then be dropped into, for example, the first torroidal housing half 15A, and the first and second torroidal housing halves 15A and 15B can be coupled by a relative rotation therebetween to engage the first and second locking arms 68 and 70.

Figure 11A:
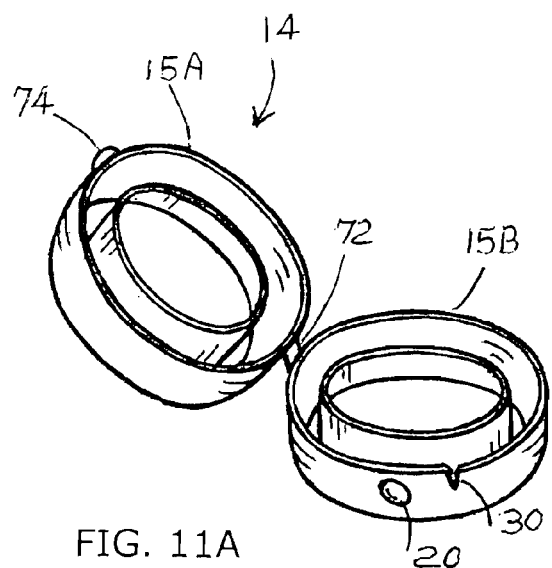
FIGS. 11A through 11C depict a potential arrangement for the accumulating ring.
Figure 11B:
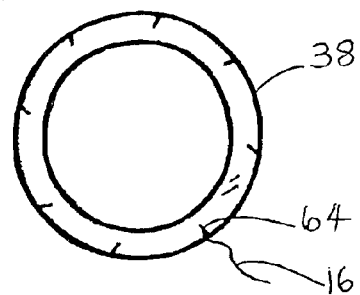
Figure 11C:
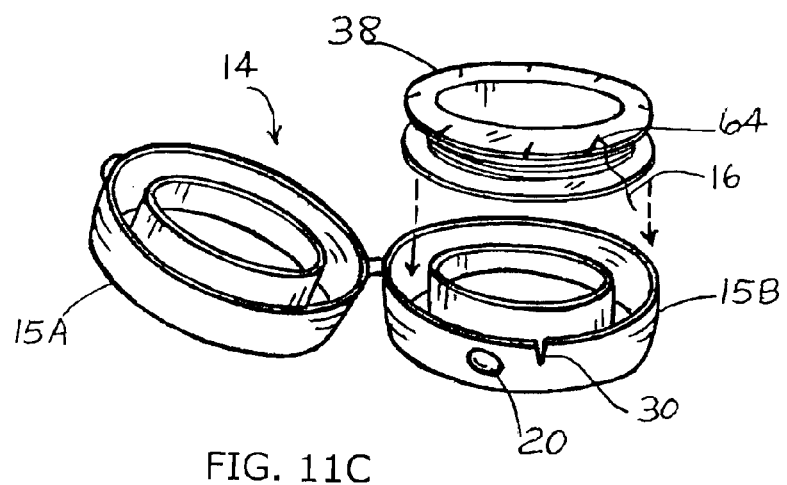

FIGS. 11A through 11C show another construction for enabling access to the inner volume of the torroidal housing 15 for allowing, among other things, the bobbin 38 to be removed and replaced and the dental floss 16 to be untangled and reattached as necessary. There, the torroidal housing 15 is again subdivided into first and second torroidal housing halves 15A and 15B. In this case, the halves 15A and 15B are coupled by a hinge 72, which can be a polymeric living hinge or any other type of hinge. Under this arrangement, a new bobbin 38 can be loaded into the torroidal housing 15 simply by first inserting an end portion of the new floss 16 into the wedge slot 64 and wrapping the floss 16 around the bobbin 38 as necessary. Then, the bobbin 38 can be inserted into one of the torroidal housing halves 15A or 15B, and the halves 15A and 15B can be closed with the floss 16 extending through the aperture 30. Although the aperture 30 is shown as being open in FIG. 11C, it could in alternative arrangements be closed. If so, the user may need to pass the floss 16 through the aperture 30 before pressing it into the wedge slot 64 and otherwise loading it into the housing halves 15A and 15B.

Figure 12:
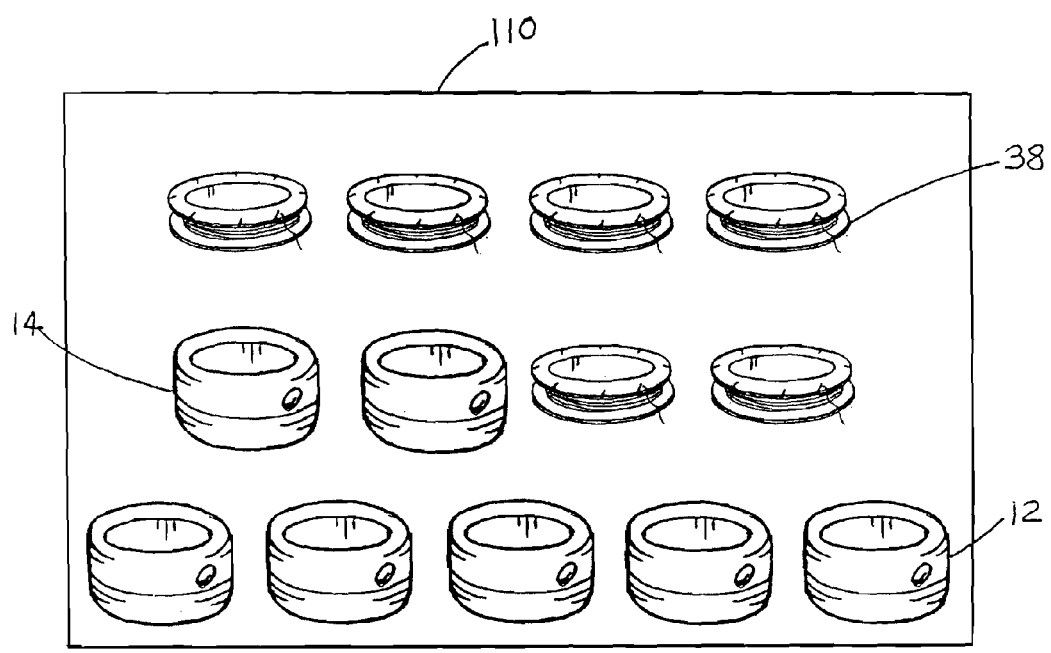
FIG. 12 depicts a packaging arrangement for embodiments of the automated flossing system.

In FIG. 12, the constituent components of the automated flossing system 10 are shown as they could be packaged for sale in a packaging arrangement 110. There, the packaging arrangement 110 includes five dispensing rings 12, two accumulating rings 14, and six stacks of multiple bobbins 38. With such an arrangement 110, the dispensing rings 12 can be used until emptied of floss 16, the disposable bobbins 38 can be used until full or otherwise ready to be discarded, and the accumulating rings 14 can each be employed to retain multiple bobbins 38 and then discarded when necessary.

As disclosed herein, the present invention for an automated flossing system 10 solves a plurality of problems that have plagued the prior art and that have contributed to making proper and consistent flossing a relative rarity among the consuming public. For example, having reference again to FIG. 1, one seeking to floss his or her teeth need only slip the dispensing ring 12 onto the middle finger 102 of, for example, his or her left hand 100 while slipping the accumulating ring 14 onto the middle finger 202 of his or her right hand 200 with a length of dental floss 16 connecting the dispensing and accumulating rings 12 and 14. Then, the user can lengthen the span of floss 16 as necessary by pressing on the activating switch 18 on the dispensing ring 12 thereby enabling sterile floss 16 to be unreeled. With a suitable length of floss 16 provided, the user can initiate flossing in the most preferred manner described above by first inserting the floss 16 between a first tooth and a second tooth and gently moving the floss 16 just to the gum line. The floss 16 can then be made into a U-shape and drawn away from the gum line. Then, the floss 16 should be shifted laterally and the next flossing step performed such as by moving the next section of floss 16 moved under the gum line and then drawn away. The process should be repeated for each side of each tooth.

Advantageously, whenever a given length of floss 16 is contaminated and fresh floss 16 is needed, the user need only press the activating buttons 18 and 20 on the dispensing ring 12 and the accumulating ring 14 to cause the soiled floss 16 to be reeled into the accumulating ring 14 and to allow sterile floss 16 to be pulled from within the dispensing ring 12. Furthermore, the use of the dispensing ring 12 and the accumulating ring 14 will avoid the uncomfortable constriction of the dental floss 16 about the user's fingers 102 and 202 that has heretofore been an inherent disadvantage during flossing. Still further, the user need not touch or otherwise be exposed to contaminated dental floss 16 as was also inherent in the prior art. Even further, by use of the dispensing ring 12 and the accumulating ring 14, the dental floss 16 is retained securely and without slippage. With these and the further advantages that can be achieved by use of automated flossing systems 10 according to the present invention, it will be appreciated that the present invention enables proper flossing to be automated and carried out conveniently, comfortably, hygienically, and, possibly most importantly, much faster thereby making it more likely to be practiced on a consistent basis by the general public.

Nonetheless, as always, there remains room for alternative constructions in the art. In this regard, one will again note the uncomfortable and possibly dangerous constriction and loss of circulation that result from wrapping floss repeatedly around a user's bare fingers. One will further note the tendency of one flossing with bare fingers to introduce contaminants and dangerous bacteria into his or her mouth from those bare fingers and the unsanitary and distasteful need for wrapping used, contaminated floss around his or her fingers. Even further, one will again note the tendency of dental floss, particularly when wet, to slip from the user's grip and otherwise to become unwound even when wrapped a number of times around the user's bare fingers. Finally, there is a need to provide an arrangement providing ease of use, added convenience, and, most of all, a greatly reduced time as compared to the manual wrapping and unwrapping of dental floss 16 in adequate lengths sufficient to avoid the cross-contamination of one's teeth.

One can attempt to limit the introduction of bacteria and other contaminants into the mouth during flossing with a thorough washing of the hands. However, unless washing is carried out in a surgical manner, harmful contaminants will remain such that contaminants will inevitably be introduced into one's mouth through use of bare fingers touching the floss and the interior of the person's mouth. For these and further reasons, a second embodiment of the present invention for oral hygiene apparatuses is described below and shown in the accompanying drawing figures.

Looking to FIG. 13, a first preferred embodiment of this further aspect of the invention comprises a finger shield arrangement, which is indicated generally at 150. As shown, the finger shield arrangement 150 can be used in supplementation of the automated flossing system 10 to avoid the need for the user's bare fingers to be placed in or around the user's mouth. In accomplishing this, this basic finger shield arrangement 150 can provide, preferably for each of the user's hands, a thumb shield 152 and an index finger shield 154 whereby the fingers that commonly must be inserted into the user's mouth can be sheathed in sterile covers. The thumb and index finger shields 152 and 154 can be separably joined by a tab fastener 156 as will be described herein. Advantageously, in addition to joining the thumb and index finger shields 152 and 154, the tab fastener 156 can be employed for pulling the finger shields 152 and 154 into a snug relationship with the user's fingers. To accomplish this most effectively, the tab 156 is angled toward the proximal portion of the user's fingers.

An alternative embodiment of the finger shield arrangement 150 is shown in FIG. 14. There, the thumb and index finger shields 152 and 154 are supplemented by a middle finger shield 158 that has a tab 160 extending therefrom. As such, this embodiment of the finger shield arrangement 150 can be used separately from the automated flossing system 10 with traditional, loose floss as is exemplified in FIG. 15. To do so, the finger shields 152, 154, and 158 would be applied to each appropriate finger and suitable lengths of floss 16 would be wrapped around the user's middle finger shields 158, and thus middle fingers. With this, traditional flossing can be carried out without the uncomfortable constriction that has commonly hindered prior art flossing practices. Advantageously, the preferred middle finger shields 158 can be reinforced with staves of wood, plastic, or any other appropriate material for further preventing the floss 16 from constricting about the user's fingers and dangerously cutting off circulation.

As shown, for example, in FIGS. 16A through 16C, the finger shield arrangement 150 can be sold and packaged in a flattened configuration. Then, the finger shields 152, 154, and 158 can be opened for use simply by placing them between the user's fingers and compressing them about their flattened dimension. With this, the finger shields 152, 154, and 158 can be formed into the open configuration shown in FIG. 16C.

Figure 17A:
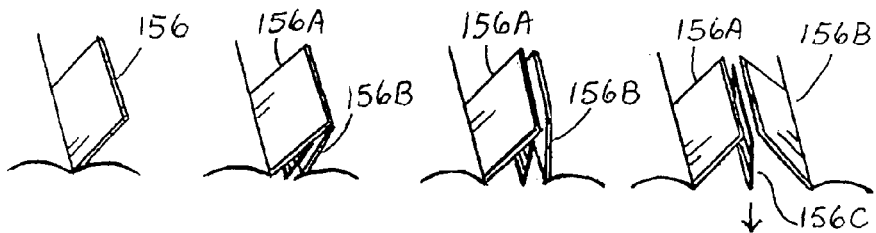
FIGS. 17A through 17C depict steps in applying the finger shields.
Figure 17B:
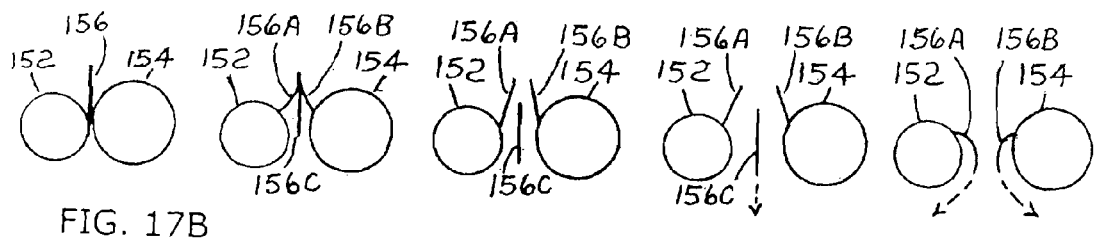
Figure 17C:
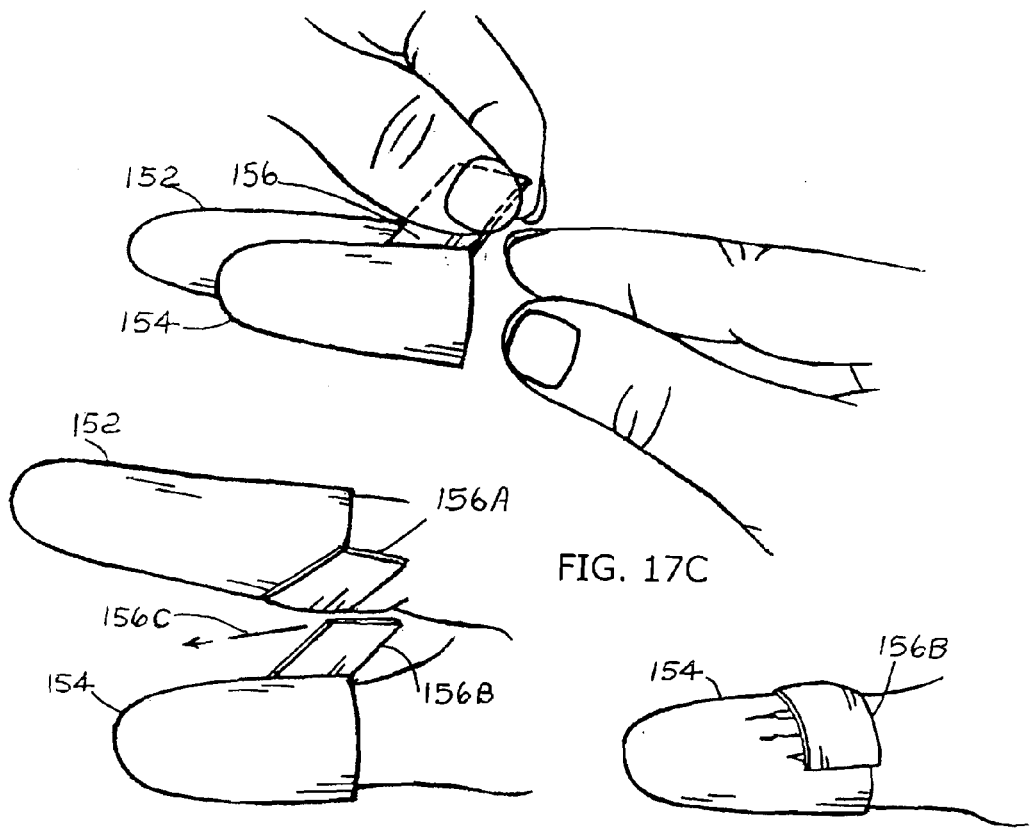

Turning to the sequential illustrations in each of FIGS. 17A through 17C, one sees how the thumb and index finger shields 152 and 154 can be applied for use. One could begin by slipping the finger shields 152 and 154 onto the appropriate thumb and index fingers. Then, the fingers could be pulled apart thereby separating the tab 156 into a first tab half 156A that remains coupled to the index finger shield 152 and a second tab half 156B that remains coupled to the thumb finger shield 154. The separation of the first and second tab halves 156A and 156B releases a separation member 156C. The first and second tab halves 156A and 156B have adhesive applied thereto while the separation member 156C comprises a smooth strip of, for example, plastic.

Figure 18:
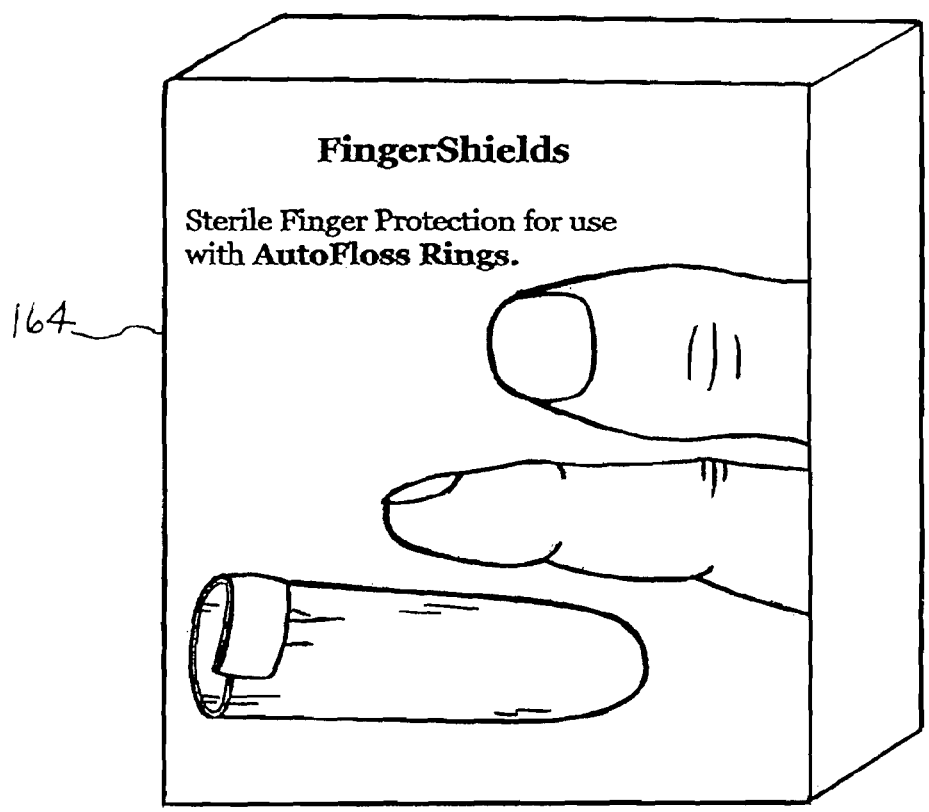
FIG. 18 is a perspective view of a possible packaging arrangement for the finger shields.

As such, the arrangement of the tab 156 is much like a pair of adhesive bandages in a facing relationship sharing a single smooth plastic removable shield. When the first and second tab halves 156A and 156B are separated, their adhesive surfaces will be exposed. As shown in the last drawings of FIGS. 17B and 17C, the tab halves 156A and 156B can then be folded over and adhered to the surface of its respective finger shield 152 or 154. In doing so, the user can if necessary use the first and second tab halves 156A and 156B as cinching members to ensure a snug fit of the finger shields 152, 154, and 158. Furthermore, the first and second tab halves 156A and 156B if desired can be adhered partially to the user's fingers thereby to ensure that the finger shields 152, 154, and 158 are retained most securely. Finally, FIG. 18 shows a possible packaging arrangement 164 for the finger shields 152, 154, and, possibly, 158. As one would expect, the finger shields 152, 154, and 158 can be manufactured and sold in a plurality of sizes.

The finger shields 152, 154, and 158 can be formed from a wide variety of materials within the scope of the present invention. For example, the finger shields 152, 154, and 158 can be manufactured to great advantage from woven cloth, paper, plastic, or any other suitable sterile material, and they could be crafted by molding, weaving, sewing, and a plurality of other methods. In certain embodiments, the finger shields 152, 154, and 158 can be impregnated with a volume of antiseptic liquid or the like, preferably suitably flavored, for providing further protection to the user against contamination both as it might otherwise be inserted into the user's mouth by his or her fingers or the like and as it might be transferred from the user's mouth to the user's fingers by contaminated floss.

While the above described dispensing and accumulating rings 12 and 14 of the automated flossing system 10 certainly achieve numerous advantages over the prior art, it must be clear that the present invention can be embodied in numerous different constructions. As will be described further below, a wide variety of arrangements can be provided for mechanically and, possibly, automatically dispensing and, additionally or alternatively, accumulating dental floss 16. The dispensing and/or accumulating arrangements can assume substantially any size, shape, or configuration including, by way of example, barrels, disks, spheres, ovals, rings, double rings, knuckles, cubes, octagons, and still further variations that can attach to, engage, or merely be retained by one finger, multiple fingers, or a user's entire hand.

The dispensing and accumulating arrangements can be disposable. Alternatively, they can be designed to be opened to be refilled, to have broken floss retied or rewound or, where applicable, evacuated of used floss and cleaned as necessary. Of course, the floss that is pre-loaded or wound onto the bobbin 38 or other retaining arrangement can be of any type including flavored, medicated, knotted, colored, waxed, of variable thickness, a tape, a ribbon, colored, or of any other type or characteristic. A motive force, such as a spring 32 or other means, can, but need not, be provided. The dispensing and/or accumulating arrangements can incorporate adjustable and/or expandable sizing arrangements that can be operable by screwing, telescoping, finger hooks, clips, bands, bracelets, and inserts, possibly combined with structures of varied initial sizing, to accommodate variably sized fingers or hands.

Figure 19A:
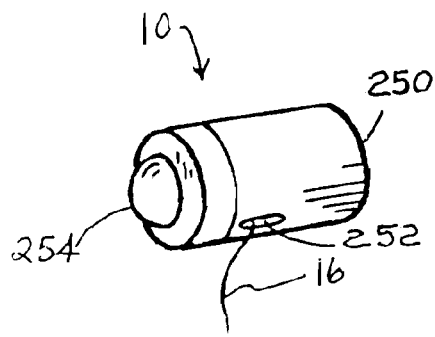
FIGS. 19A through 19C are perspective views of a freely held automated flossing system under the present invention.
Figure 19B:
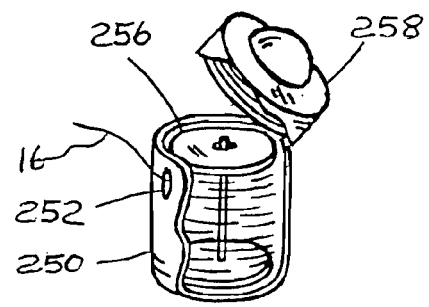
Figure 19C:
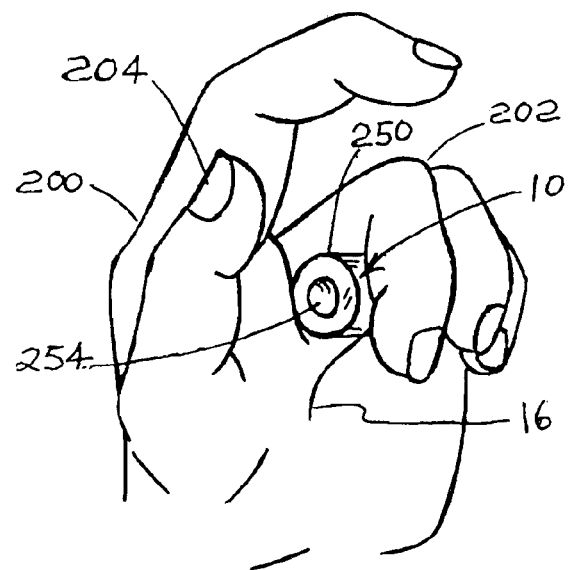

With these things in mind, one can look to FIGS. 19A through 19C where an automated flossing system 10 is founded on a shell 250, which in this embodiment comprises a barrel shell 250. The barrel shell 250 rotatably retains a bobbin 256 onto which a length of dental floss 16 is wound. The barrel shell 250 has a hinged cap 258 to allow access to the bobbin 256. As such, where the barrel shell 250 is used to dispense new dental floss 16, the entire bobbin 256 can be removed when emptied of dental floss 16 and replaced with a new, fully loaded bobbin 256 or to have new dental floss 16 wound thereon. Alternatively, where the bobbin 256 is used to accumulate used dental floss 16, the bobbin 256 can be removed to be discarded or to have used floss 16 removed therefrom to allow further usage of the original bobbin 256.

Dental floss 16 passes from within the inner volume of the barrel shell 250 through a slot aperture 252. The ability of the bobbin 256 to rotate within the barrel shell 250 can be controlled by an activating trigger 254, which in this case comprises a button 254 at an end of the barrel shell 250. The activating trigger 254 can simply release the bobbin 256 to enable it to rotate in response to a user's pulling on the dental floss 16. Alternatively, the bobbin 256 and the barrel shell 250 can be spring loaded to cause the bobbin 256 to rotate to allow, for example, dental floss 16 to be reeled onto the bobbin 256, to allow dental floss 16 to be dispensed from the bobbin 256, or to allow a user to draw dental floss 16 from the barrel shell 250 against a countervailing spring force.

Under this arrangement, the barrel shell 250 can be disposed, for example, as is shown in FIG. 19C within the palm of the user's hand 200 with one or more of the user's fingers 202 retaining the barrel shell 250 with the activating trigger 254 disposed proximal to the user's thumb 204. With this, a user can press on the activating trigger 254 with his or her thumb 204 to enable dental floss 16 to be dispensed or accumulated in a most convenient manner.

While the barrel shell 250 can certainly be retained as described above, certain embodiments of the invention contemplate the provision of a means for retaining the barrel shell 250 relative to a user's hand 200. For example, in FIGS. 20A through 20D, the automated flossing system 10 further incorporates one or more means for retaining the barrel shell 250 relative to a user's fingers 202. In FIG. 20A, a ring member 260 is fixed by any appropriate method to the barrel shell 250 such that it can be slipped onto one of the user's fingers 202 as is shown in FIG. 20D with the barrel shell 250 disposed either within the user's palm as shown in FIG. 20D or with the barrel shell 250 disposed to the outside of the user's hand.

The ring 260 can be of a fixed circumference as is shown in FIG. 20A. Alternatively, the automated flossing system 10 can include a means for adjusting the circumference of the ring 260 as is first shown in FIG. 20B. There, the adjusting means 262 comprises a beaded first strap section of the ring 260 in combination with a jawed second strap section of the ring 260. Under such a construction, a user can adjust the effective circumference of the ring 260 by a selective engagement of the jawed second strap section with the beaded first strap section. In the alternative arrangement of FIG. 20C, first and second rings 260A and 260B are provided for engaging two fingers 202 of a user to enable the barrel shell 250 to be retained most securely and comfortably. The effective circumferences of the first and second rings 260A and 260B can be adjusted by an is adjusting means 262 comprising a beaded first strap section of the first ring 260A, a jawed second strap section of the second ring 260B, and a jawed central member that completes each of the first and second rings 260A and 260B.

Although the ring 260 or the rings 260A and 260B can be fixed to the barrel shell 250 as shown in FIGS. 20A through 20D, such as by being formed integrally therewith, the ring 260 or rings 260A and 260B alternatively can be removably and replaceably coupled to the barrel shell 250. For example, as is shown in FIGS. 21A through 21C, the ring 260 or rings 260A and 260B could be coupled to the barrel shell 250 by means of a barrel engaging ring 264 that is fixed to the ring 260, such as by being formed integrally therewith or by being fixed or rotatably coupled thereto. As FIG. 21C shows most clearly, the barrel engaging ring 264 can be employed to engage the barrel shell 250 in a frictional relationship thereby to enable the barrel shell 250 to be removed as necessary or desirable.

In any case, it will be realized that numerous different arrangements could be provided as adjusting means 262 beyond the beaded/jaw arrangement shown, for example, in FIGS. 20B, 20C, and 21E. For example, as FIGS. 21B and 21D show, the effective circumference of the ring 260 can be adjusted by an adjusting means 262 comprising a first strap section with a plurality of apertures and a second strap section with an engaging protuberance on a second strap section. Still further, as is shown in FIG. 21F, the adjusting means 262 could comprise a threaded arrangement, such as a bolt in combination with a wing nut, coupling a first strap section with a second strap section.

Of course, other means for retaining the barrel shell 250 relative to a user's hand 200 are fully within the scope of the present invention. For example, as is shown in FIGS. 22A through 22E, an opposed hook arrangement 268 could be retained by a central post 266 such that a user's fingers 202 could be retained between the opposed hooks of the opposed hook arrangement 268 and the barrel shell 250. The barrel shell 250 could be disposed to the palm side of the user's hand 200 or to the outside of the hand 200. The central post 266 could be fixed to the barrel shell 250 as by being formed integrally therewith, by being coupled thereto, or by means of a barrel engaging ring 264 as discussed previously.

The central post 266 could be of a substantially fixed length as is shown in FIG. 22C such that the user's fingers 202 could be slid or snapped into place to induce a deflection and frictional engagement of the opposed hook arrangement 268 and the user's fingers 202. Alternatively, the central post 266 could be made extensible and retractable by any appropriate means such that it can extend to accommodate a user's fingers 202 and then can compress thereabout to ensure a secure yet comfortable frictional engagement. For example, as is shown in FIGS. 22A and 22B, there could be a reciprocatable male/female engagement 270 in combination with a biasing member 272, such as a spring, a rubber member, or any other suitable means, for biasing the opposed hook arrangement 268 to a retracted position. Still further, the central post 266 can be resiliently deformable, such as by being curved as is shown in FIGS. 22F and 22G, by being coiled, or by any other suitable arrangement, such that a user can deform the central post 266 to accommodate his or her fingers 202 and the central post 266 can bias the opposed hook arrangement 268 into frictional engagement with the user's fingers. To ensure that the opposed hook arrangement 268 comfortably engages the user's fingers, it can be hingedly coupled to central post 266 by a hinge arrangement 265.

In further refinements of the invention as exemplified in FIGS. 23A through 23G, the central post 266 could act as a conduit for enabling dental floss 16 to travel from the barrel shell 250, between the user's fingers 202, and therebeyond for use in flossing or for accumulation after flossing. Although it need not, the central post 266 could additionally incorporate the activating trigger 254 at the distal end thereof. For example, as is shown in FIGS. 23A, 23B, 23C, and 23H, the central post 266 could be engageable with the barrel shell 250 by a barrel engaging ring 264 and could have the dental floss 16 threaded through the proximal end of the central post 266 until it exits the distal end thereof. One will note from FIGS. 23A and 23H that the barrel engaging ring 264 could be a complete annular structure or it could comprise a semicircular structure for being snapped over or otherwise engaged with the barrel shell 250. The central post 266 again could be of a fixed length, extendable and retractable, and/or curved or coiled to exhibit frictionally engaging spring tension.

Under this arrangement, the automated flossing system 10 could be engaged with the fingers 202 of the user's hand 200 as is shown in FIGS. 23C and 23D with the barrel shell 250 disposed to the outside of the user's hand 200 and with the dental floss 16 and the activating trigger 254 disposed to the palm side of the user's hand 200. With this, the activating trigger 254 can be readily pressed by the user's thumb 204 to allow dental floss 16 to be dispensed from or accumulated into the barrel shell 250.

Figure 24A:
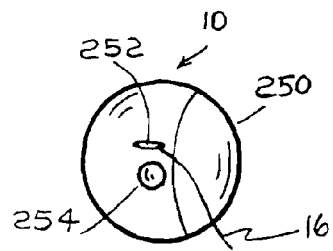
FIGS. 24A through 24F are perspective views of further embodiments of accumulating/dispensing arrangements.
Figure 24B:
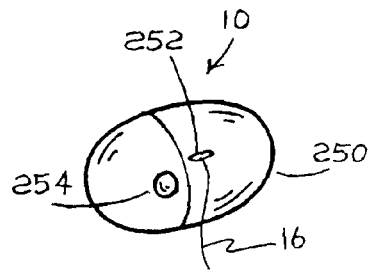
Figure 24C:
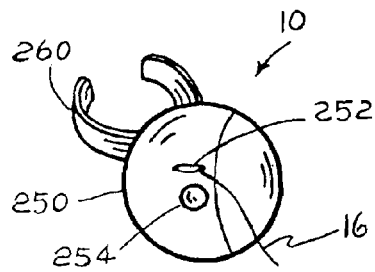
Figure 24D:
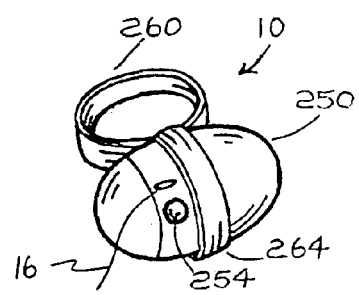
Figure 24E:
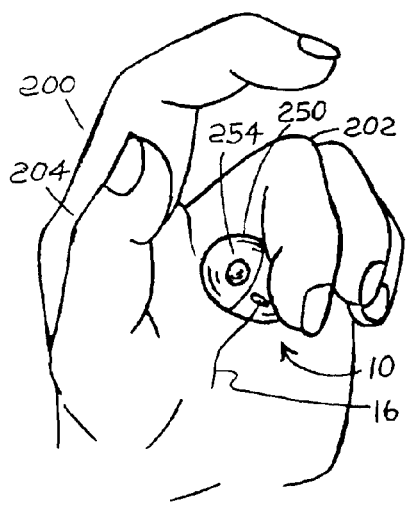
Figure 24F:
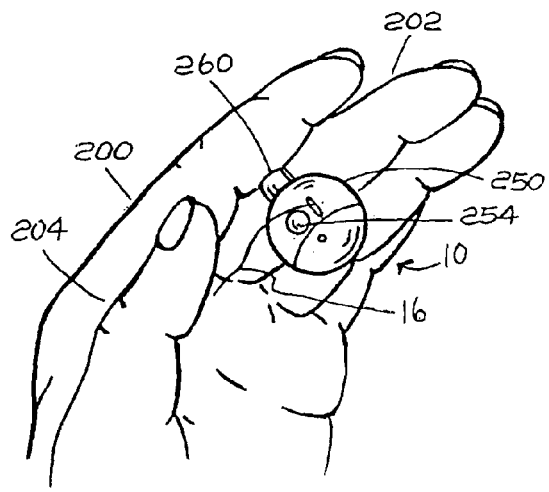

It will be appreciated, of course, that the particular shape of the shell 250 can vary nearly infinitely within the scope of the invention. For example, as is shown in FIGS. 24A, 24C, and 24F, the shell 250 can comprise a spherical shell 250. As FIGS. 24B, 24D, and 24E illustrate, the shell 250 can alternatively take the form of an egg-shaped shell 250. In each case, the shell 250 can be freely retained in the user's palm as FIGS. 24A, 24B, and 24E show. Alternatively, the shell 250 can be retained relative to the user's fingers 202 by a ring 260, which can be a complete ring 260 as is shown in FIG. 24D or a partial ring 260 as is shown in FIG. 24C. Where there is a partial ring 260, it can be adjustable in circumference as previously described. In any case, the ring 260 can be fixed directly to the shell 250 as FIG. 24C shows or it can be removably and replaceably coupled thereto, such as by a barrel engaging ring 264 as FIG. 24D depicts. As before, the dental floss 16 can exit the shell 250 through an aperture 252 and can be allowed to be dispensed or accumulated by operation of an activating trigger 254.

The versatility of the invention can be further appreciated with reference to FIGS. 25A through 25I where the automated flossing system 10 has a disk-shaped shell 250. In the most basic embodiment of FIGS. 25A and 25H, the disk-shaped shell 250 is designed to be freely retained in the palm of the user's hand 200. In FIG. 25B, however, a central post 266 projects from the shell 250 to act as a conduit for allowing dental floss 16 to pass therethrough and to retain an opposed hook arrangement 268 for engaging the user's fingers 202 as is shown in FIG. 25F. The central post 266 again has an activating trigger 254 at the distal end thereof for enabling a ready actuation of the automated flossing system 10 by, for example, the user's thumb 204. In a variant of the embodiment of FIG. 25B, the embodiment of FIG. 25C further includes a proximal opposed hook arrangement 267 for further engaging a user's fingers 202. In the embodiments of FIGS. 25B and 25C, the shell 250 would be likely to be disposed to the outside of the user's hand 200 as is shown in FIG. 25G. One will further note that, in the embodiments of FIGS. 25A, 25C, 25H, and 25I, the dental floss 16 exits the shell 250 laterally as compared to the central exiting depicted in numerous other embodiments shown herein.

In the embodiments of FIGS. 25D and 25E, the shell 250 can be retained relative to a user's hand 200 by a ring 260, which can be a complete ring 260 as is shown in FIG. 25D or a partial ring as is shown in FIG. 25E, which again could be adjustable in circumference employing the previously described and further arrangements. The activating trigger 254 can be disposed directly on the shell 250, and the dental floss 16 can exit directly from the shell 250 also. Under such a construction, the shell 250 would be likely to be disposed within the palm of the user's hand 200 as is shown in FIG. 25I.

Figure 26A:
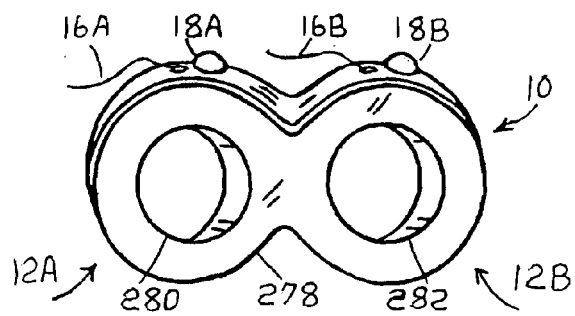
FIGS. 26A through 26C are perspective views of an automated flossing system with unitized dual accumulating/dispensing arrangements.
Figure 26B:
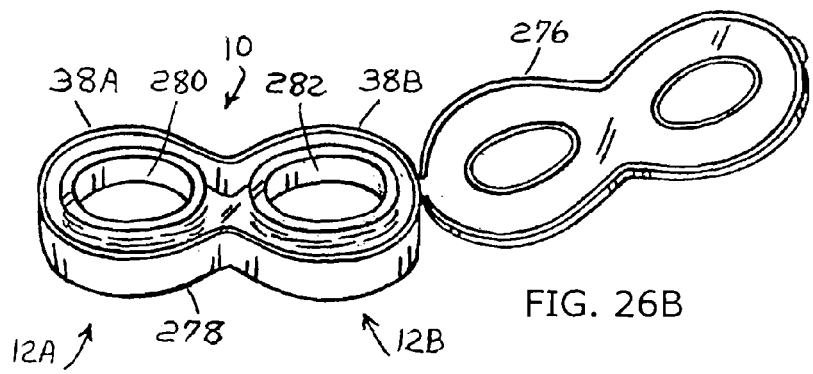
Figure 26C:
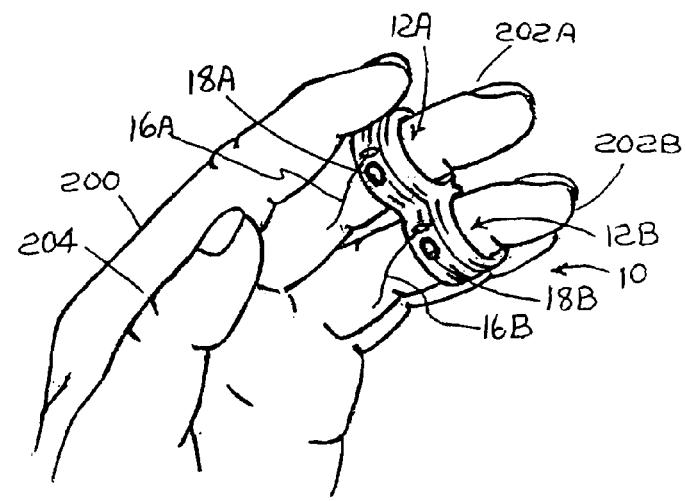

FIGS. 26A through 26C illustrate still another variation of the automated flossing system 10. There, first and second rings 12A and 12B are coupled to one another thereby to provide dual means for dispensing or accumulating dental floss 16. In this case, the first and second rings 12A and 12B happen to be integrally formed with a unitary base housing 278 and a unitary cap member 276, each having the general form of a figure eight with first and second finger receiving apertures 280 and 282 thereby being provided. The first and second rings 12A and 12B rotatably retain first and second bobbins 38A and 38B respectively for dispensing or accumulating first and second strands of dental floss 16A and 16B. First and second activating triggers 18A and 18B are operably associated with the first and second rings 12A and 12B for inducing a reeling in or dispensing of dental floss 16A and 16B.

Under this arrangement, a user can slide his or her first and second fingers 202A and 202B into the first and second apertures 280 and 282 of the first and second rings 12A and 12B of the automated flossing system 10 as is shown in FIG. 26C. When the automated flossing system 10 is so disposed, the user can enable the dispensation or accumulation of dental floss 16A or 16B by a selective depression of one or both activating triggers 18A or 18B. When either or both bobbins 38A or 38B are emptied of new floss or full of used floss as the case may be, the cap member 276 can be opened to allow access to the bobbins 38A and 38B for removal, replacement, refilling, or emptying.

Figure 27A:
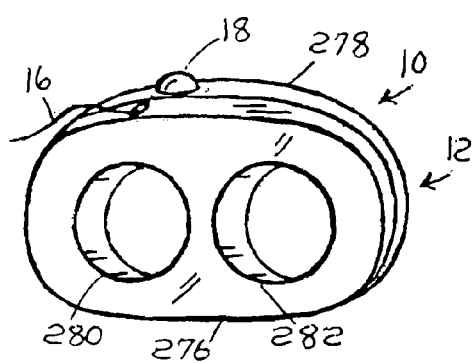
FIGS. 27A through 27C are perspective views of a further embodiment of an automated flossing system with first and second finger apertures.
Figure 27B:
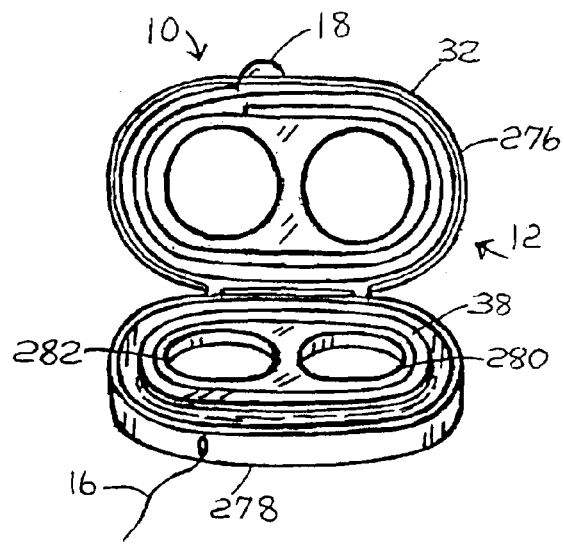
Figure 27C:
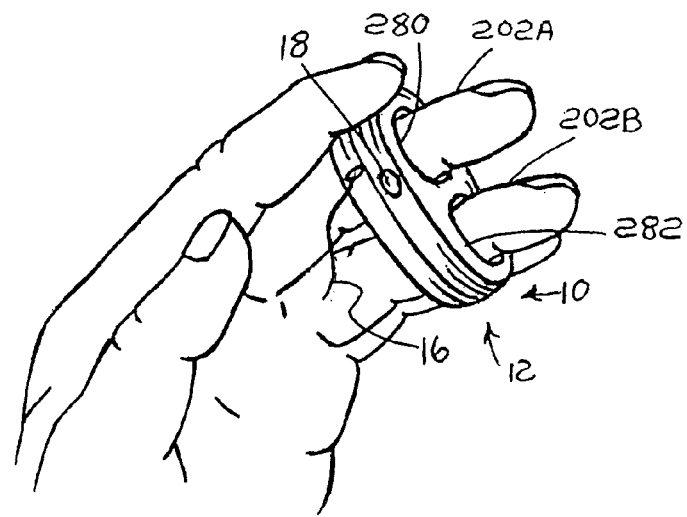

Still further, FIGS. 27A through 27C show an embodiment of the automated flossing system 10 where a unitary dispensing or accumulating ring 12 acts as a knuckle arrangement with first and second apertures 280 and 282 and a central body portion for spanning two fingers 202A and 202B. The ring 12 has a flexible bobbin 38 that encircles both apertures 280 and 282 within a housing 278 that is enclosed by a cap member 276. An effective rotation of the bobbin 38 can be propelled or resisted by a spring member 32, which in this case is incorporated into the cap member 276. An activating trigger 18 again allows a user to enable a selective rotation of the bobbin 38 to allow a corresponding dispensing or accumulating of dental floss 16.

Figure 28A:
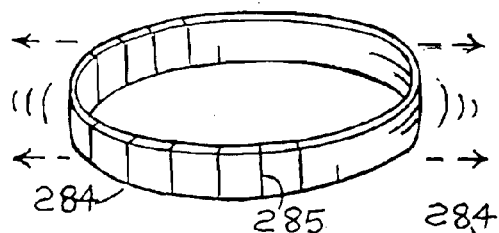
FIGS. 28A through 28F are perspective views of yet another means for retaining an accumulating/dispensing arrangement under the present invention.
Figure 28B:
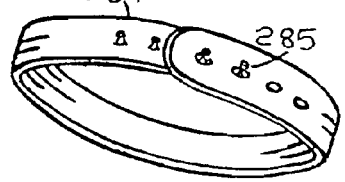
Figure 28C:
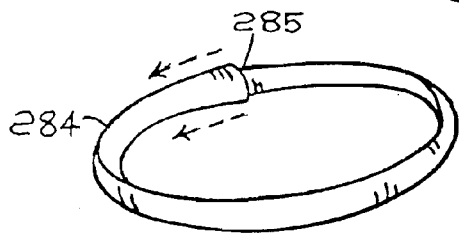
Figure 28D:
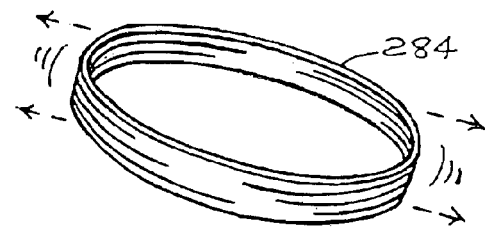
Figure 28E:
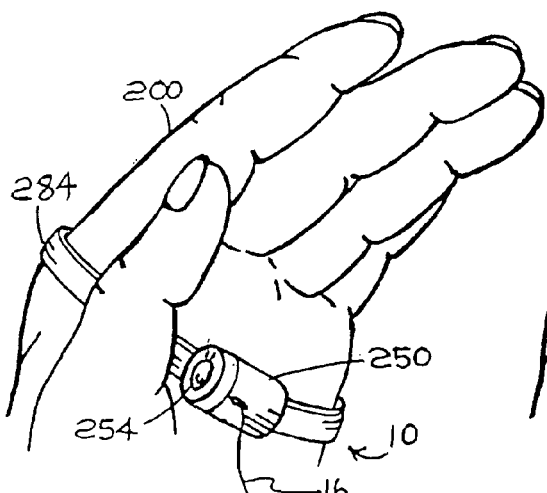
Figure 28F:
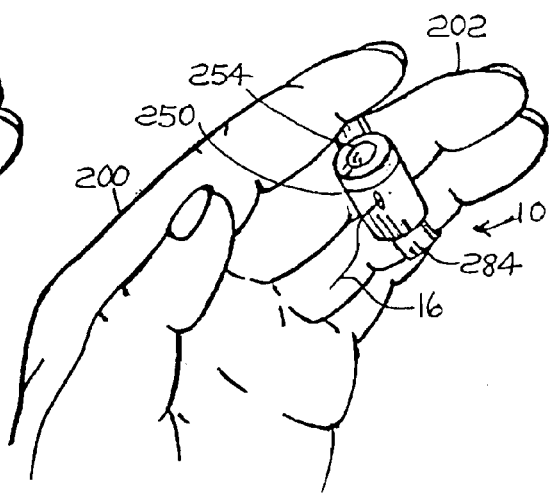

Even further still, FIGS. 28A through 28F make clear that embodiments of the automated flossing system 10 can be crafted for being securely retained relative to a user's hand by a band member 284. As FIGS. 28A through 28D show, the circumference of the band member 284 can be varied by numerous different methods. For example, in FIG. 28A, the circumference of the band member 284 can be expanded by exploitation of a means 285 comprising a plurality of spring loaded couplings. In FIG. 28B, the circumference of the band member 284 can be varied by a means 285 comprising an aperture and protuberance combination. Alternatively, the circumference of the band member 284 can be varied by use of a means 285 comprising a single spring loaded coupling. Even further, the band member 284 can vary in circumference simply by being formed from a resilient material, such as rubber. Under such constructions, the band member 284 can be coupled to a housing 250 by any appropriate method and the completed automated flossing system 10 can be retained in a variety of dispositions relative to a user's hand 200, such as by surrounding and frictionally engaging the palm portion of a user's hand 200 as is shown in FIG. 28E or by surrounding and frictionally engaging one or more fingers 202 of the user's hand 200 as FIG. 28F illustrates.

From the foregoing, it will be clear that the present invention has been shown and described with reference to certain preferred embodiments that merely exemplify the broader invention revealed herein. Certainly those skilled in the art can conceive of alternative embodiments. For instance, those with the major features of the invention in mind could craft embodiments that incorporate those major features while not incorporating all of the features included in the preferred embodiments.

With the foregoing in mind, the following claims are intended to define the scope of protection to be afforded the inventor, and the claims shall be deemed to include equivalent constructions insofar as they do not depart from the spirit and scope of the present invention. A plurality of the following claims may express certain elements as a means for performing a specific function, at times without the recital of structure or material. As the law demands, these claims shall be construed to cover not only the corresponding structure and material expressly described in this specification but also equivalents thereof.

I claim as deserving the protection of Letters Patent:

1. A dental hygiene apparatus comprising:
   a floss retaining member comprising a first ring with an aperture for receiving a finger of a user and a means for retaining dental floss within the ring, a second ring with an aperture for receiving a finger of a user, and a means for retaining dental floss within the second ring whereby the floss retaining member comprises floss retaining knuckles; and
   a means for enabling a transfer of dental floss relative to the floss retaining member.

2. The dental hygiene apparatus of claim 1 further comprising a means for varying size of the aperture in the ring.

3. The dental hygiene apparatus of claim 1 wherein the means for retaining dental floss relative to the floss retaining member comprises a floss retaining bobbin retained relative to the ring and a floss retaining bobbin retained relative to the second ring.

4. The dental hygiene apparatus of claim 1 wherein the means for retaining dental floss relative to the floss retaining member comprises a bobbin that surrounds the apertures in the ring and the second ring.

5. The dental hygiene apparatus of claim 4 wherein the means for enabling a transfer of dental floss relative to the floss retaining member comprises an activating trigger operably associated with the floss retaining member.

6. The dental hygiene apparatus of claim 1 wherein the means for retaining dental floss relative to the floss retaining member comprises a floss retaining bobbin and wherein the means for enabling a transfer of dental floss relative to the floss retaining member comprises an activating switch in combination with a means for rotating the floss retaining bobbin.

7. The dental hygiene apparatus of claim 6 wherein the activating means further comprises a means for selectively engaging the activating switch with the floss retaining bobbin.

8. The dental hygiene apparatus of claim 6 wherein the means for rotating the floss retaining bobbin comprises a coil spring and further comprising a means for enabling a winding of the coil spring.

9. The dental hygiene apparatus of claim 1 further comprising a scrubber element retained relative to the floss retaining member wherein the scrubber element is removable and replaceable relative to the floss retaining member.

10. The dental hygiene apparatus of claim 1 wherein the floss retaining shell is disk-shaped and wherein the activating trigger is disposed on the floss retaining shell.

* * * * *